United States Patent
Farrand et al.

(10) Patent No.: US 6,913,710 B2
(45) Date of Patent: Jul. 5, 2005

(54) REACTIVE MESOGENIC BENZODITHIOPHENES

(75) Inventors: Louise Farrand, Blandford Forum (GB); Martin Heeney, Southampton (GB); Steven Tierney, Southampton (GB); Mark Giles, Southampton (GB); Marcus Thompson, Hamshire (GB); Maxim Shkunov, Southampton (GB); David Sparrowe, Bournemouth Dorset (GB); Iain McCulloch, Hants (GB)

(73) Assignee: Merck Patent GmbH, Darmstadt (DE)

( * ) Notice: Subject to any disclaimer, the term of this patent is extended or adjusted under 35 U.S.C. 154(b) by 20 days.

(21) Appl. No.: 10/421,873

(22) Filed: Apr. 24, 2003

(65) Prior Publication Data

US 2003/0209692 A1 Nov. 13, 2003

(30) Foreign Application Priority Data

Apr. 24, 2002 (EP) .......................................... 02009083

(51) Int. Cl.[7] .............................................. C09K 19/52
(52) U.S. Cl. ........................... 252/299.61; 252/299.62; 549/43; 549/45; 549/59; 549/83
(58) Field of Search ............................ 549/29–31, 41, 549/59, 43, 83, 45, 47, 48; 428/1.1; 252/299.01, 299.2, 299.3, 299.62, 299.61

(56) References Cited

U.S. PATENT DOCUMENTS

| 5,198,153 A | 3/1993 | Angelopoulos et al. |
| 5,892,244 A | 4/1999 | Tanaka et al. |
| 5,998,804 A | 12/1999 | Suh et al. |

FOREIGN PATENT DOCUMENTS

| DE | 195 04 224 A1 | 8/1995 | |
| EP | 0 261 712 A1 | 3/1988 | |
| EP | 0 528 662 A1 | 2/1993 | |
| EP | 0 889 350 A1 | 1/1999 | |
| JP | 63-122727 | * 5/1988 | ........... C08G/61/12 |
| JP | 07-056368 | * 3/1995 | ............ G03G/5/06 |
| WO | WO 93/22397 A1 | 11/1993 | |
| WO | WO 95/22586 A1 | 8/1995 | |
| WO | WO 96/21659 A1 | 7/1996 | |
| WO | WO 97/00600 A2 | 1/1997 | |
| WO | WO 00/79617 A1 | 12/2000 | |

OTHER PUBLICATIONS

English Language translation of Amano (done by computer on Jun. 14, 2004).*
English Language Abstract of Kimura (done by computer on Jun. 14, 2004).*

* cited by examiner

*Primary Examiner*—Mark F. Huff
*Assistant Examiner*—Jennifer R. Sadula
(74) *Attorney, Agent, or Firm*—Millen, White, Zelano, Branigan, P.C.

(57) ABSTRACT

The invention relates to new reactive mesogenic benzodithiophene derivatives, their use as semiconductors or charge transport materials, in optical, electro-optical or electronic devices like for example liquid crystal displays, optical films, organic field effect transistors (FET or OFET) for thin film transistor liquid crystal displays and integrated circuit devices such as RFID tags, electroluminescent devices in flat panel displays, and in photovoltaic and sensor devices, and to a field effect transistor, light emitting device or ID tag comprising the reactive mesogenic benzodithiophenes.

50 Claims, No Drawings

REACTIVE MESOGENIC BENZODITHIOPHENES

FIELD OF THE INVENTION

The invention relates to new reactive mesogenic benzodithiophene derivatives. The invention further relates to their use as semiconductors or charge transport materials, in optical, electro-optical or electronic devices like for example liquid crystal displays, optical films, organic field effect transistors (FET or OFET) for thin film transistor liquid crystal displays and integrated circuit devices such as RFID tags, electroluminescent devices in flat panel displays, and in photovoltaic and sensor devices. The invention further relates to a field effect transistor, light emitting device or ID tag comprising the reactive mesogenic benzodithiophenes.

BACKGROUND AND PRIOR ART

Organic materials have recently shown promise as the active layer in organic based thin film transistors and organic field effect transistors [see H. E. Katz, Z. Bao and S. L. Gilat, *Acc. Chem. Res.*, 2001, 34, 5, 359]. Such devices have potential applications in smart cards, security tags and the switching element in flat panel displays. Organic materials are envisaged to have substantial cost advantages over their silicon analogues if they can be deposited from solution, as this enables a fast, large-area fabrication route.

The performance of the device is principally based upon the charge carrier mobility of the semi-conducting material and the current on/off ratio, so the ideal semiconductor should have a low conductivity in the off state, combined with a high charge carrier mobility ($>1 \times 10^{-3}$ $cm^2V^{-1}$ $s^{-1}$). In addition, it is important that the semi-conducting material is relatively stable to oxidation i.e. it has a high ionisation potential, as oxidation leads to reduced device performance.

A known compound which has been shown to be an effective p-type semiconductor for OFETs is pentacene [see S. F. Nelson, Y. Y. Lin, D. J. Gundlach and T. N. Jackson, *Appl. Phys. Lett.*, 1998, 72,1854]. When deposited as a thin film by vacuum deposition, it was shown to have carrier mobilities in excess of 1 $cm^2$ $V^{-1}$ $s^{-1}$ with very high current on/off ratios greater than $10^6$. However, vacuum deposition is an expensive processing technique that is unsuitable for the fabrication of large-area films.

Regular poly(3-hexylthiophene) has been reported with charge carrier mobility between $1 \times 10^{-5}$ and $4.5 \times 10^{-2}$ $cm^2$ $V^{-1}$ $s^{-1}$, but with a rather low current on/off ratio between 10 and $10^3$ [see Z. Bao et al., *Appl. Phys. Lett.* 1997, 78, 2184]. In general, poly(3-alkylthiophenes) show improved solubility and are able to be solution processed to fabricate large area films. However, poly(3-alkylthiophenes) have relatively low ionisation potentials and are susceptible to doping in air [see H. Sirringhaus et al., *Adv. Solid State Phys.* 1999, 39,101].

It was an aim of the present invention to provide new organic materials for use as semiconductors or charge transport materials, which are easy to synthesise, have high charge mobility and good processability. The materials should be easily processable to form thin and large-area films for use in semiconductor devices. Other aims of the invention are immediately evident to those skilled in the art from the following description.

It has been reported in the literature that benzo[1,2-b:4,5-b'] dithiophene, hereinafter also shortly referred to as benzodithiophene with the following structure

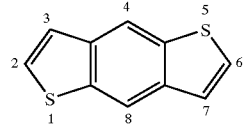

has a high charge carrier mobility and is useful as organic semiconductor. Benzodithiophene monomers or dimers, oligo- or polymers formed thereof and their use as an organic semiconductors have been described for example in Kossmehl et al., *Makromol. Chem.* 1983,184(3), 627–50, Katz et al., *J. Mater. Chem.* 1997, 7(3), 369–76, Laquindanum et al.,*Adv. Mater.* 1997, 9(1), 36–39 and in U.S. Pat. No. 5,625,199.

In particular the dimeric bisbenzodithiophene has been shown to exhibit high charge carrier mobilities of 0.04 $cm^2V^{-1}s^{-1}$. Its structure has flatter conformation than e.g. α-sexithiophene with comparable size. This enables compressed molecular packing and strong intermolecular interactions, which is favourable for compact stacking of the material and results in π—π-overlap and hence makes this compound an effective charge transport materials with high carrier mobilities. However, bisbenzodithiophene has a very high melting point over 400° C. and very low solubility in organic solvents, so that it cannot be readily solution processed and can only be vacuum deposited.

Therefore, another aim of the invention was to provide benzodithiophenes that are more easily processible in the manufacture of semiconductor devices.

SUMMARY OF THE INVENTION

It was found that the above aims can be achieved by providing reactive mesogenic benzodithiophenes, hereinafter also referred to as reactive benzodithiophene mesogens, according to the present invention. They comprise a central mesogenic core comprising one or more benzodithiophene groups, and optionally comprising further unsaturated organic groups that form a conjugated system together with the benzodithiophene groups, said mesogenic core being linked, optionally via a spacer group, to one or more reactive groups. The reactive mesogenic benzodithiophenes can induce or enhance liquid crystal phases or are liquid crystalline themselves. They can be oriented in their mesophase and the polymerisable group can be polymerised or crosslinked in situ to form polymer films with a high degree of order, thus yielding improved semiconductor materials with high stability and high charge carrier mobility.

A further aspect of the invention relates to liquid crystal polymers, in particular liquid crystal side chain polymers obtained from the reactive mesogenic benzodithiophenes according to the present invention, which are then further processed e.g. from solution as thin layers for use in semiconductor devices.

DEFINITION OF TERMS

The term 'liquid crystal or mesogenic material' or 'liquid crystal or mesogenic compound' should denote materials or compounds comprising one or more rod-shaped, board-shaped or disk-shaped mesogenic groups, i.e. groups with the ability to induce liquid crystal phase behaviour. Liquid crystal compounds with rod-shaped or board-shaped groups are also known in the art as 'calamitic' liquid crystals. Liquid crystal compounds with a disk-shaped group are also known in the art as 'discotic' liquid crystals. The compounds or materials comprising mesogenic groups do not necessarily have to exhibit a liquid crystal phase themselves. It is also possible that they show liquid crystal phase behaviour only in mixtures with other compounds, or when the mesogenic compounds or materials, or the mixtures thereof, are polymerised.

The term 'reactive group' or 'reactive compound' includes compounds or groups that are capable of participating in a polymerisation reaction, like radicalic or ionic polymerisation from unsaturated functionality, polyaddition or polycondensation, as well as compounds or groups that are capable of being grafted for example by condensation or addition to a reactive polymer backbone in a polymeranaloguous reaction.

The term 'film' includes self-supporting, i.e. free-standing, films that show more or less pronounced mechanical stability and flexibility, as well as coatings or layers on a supporting substrate or between two substrates.

The invention relates to reactive mesogenic benzodithiophenes, comprising a central mesogenic core that comprises one or more benzodithiophene groups and optionally comprises further unsaturated organic groups that form a conjugated system together with the benzodithiophene groups, said mesogenic core being linked, optionally via a spacer group, to one or more reactive groups.

The invention also relates to the use of reactive mesogenic benzodithiophenes as semiconductors or charge transport materials, in particular in optical, electro-optical or electronic devices, like for example in field effect transistors as components of integrated circuitry, as thin film transistors in flat panel display applications or RFID tags, or in semiconducting components for organic light emitting diode (OLED) applications such as electroluminescent displays or backlights of flat panel displays, for photovoltaic or sensor devices, or as light-modulating components for liquid crystal displays, optical films or other optical or electrooptical devices.

The invention also relates to a field effect transistor, for example as a component of integrated circuitry, as a thin film transistor in flat panel display applications, or in an RFID tag, comprising one or more reactive or polymerised mesogenic benzodithiophenes according to the present invention.

The invention also relates to a semi-conducting component, for example in OLED applications like electroluminescent displays or backlights of flat panel displays, in photovoltaic or sensor devices, comprising one or more reactive or polymerised mesogenic benzodithiophenes according to the present invention.

DETAILED DESCRIPTION OF THE INVENTION

The reactive benzodithiophenes according to the present invention provide several advantages over prior art materials

- by adding substituent chains and other groups to the benzodithiophene core they can be made more soluble, thus being suitable for spin coating or solution coating techniques, rather than vacuum deposition, to prepare thin films for use e.g. in electronic devices such as transistors,
- they can be made mesogenic or liquid crystalline, thus exhibiting a higher degree of order that leads to particularly high charge carrier mobility, in particular when being aligned in their mesophase into macroscopically ordered orientation
- their macroscopic mesophase properties can be frozen in by in situ polymerisation,
- they combine the properties of a semi-conducting material with those of a mesogenic material to give novel materials with a rigid, planar conjugated core and a flexible chain to increase solubility and to decrease the melting point, which show high charge carrier mobility when being aligned in their mesophase.

The inventive reactive mesogenic benzodithiophenes are useful as charge transport semiconductors, in that they have high carrier mobilities. In particular, the introduction of side groups to the conjugated rings bonded to the benzodithiophene core improves their solubility and therefore their solution processability. In the compounds according to the present invention, the benzodithiophene group is a mesogenic group or part of a mesogenic group. These compounds are therefore particularly useful as semiconductors or charge transport materials, as they can be processed while in the highly ordered mesophase morphology, and readily aligned by conventional techniques in a preferred direction. Both smectic and nematic mesophase ordering allows close packing of molecular pi-electron systems, which maximises intermolecular charge transfer which occurs through a hopping mechanism between adjacent molecules. This ordered, and oriented microstructure can be permanently "frozen-in" by polymerising the mesogens, which can also create a structure with long range order, or "monodomain". Formation of a monodomain also maximises charge transfer by eliminating charge trap sites at grain boundaries, while the polymerisation also improves the mechanical properties of the film. Further, by cross-linking the mesogens, a highly stable structure results, which has an additional advantage of being impervious to subsequent processing solvents during device fabrication, thus allowing a wider range of solvents to be used in deposition of the next layer of the device by solution techniques. In addition, it is often observed that this cross-linking further densities the film, leading to smaller intermolecular distances and improved charge transport.

It is also possible to copolymerise benzodithiophenes of the present invention with other mesogenic or liquid crystal monomers that are known from prior art, or with other reactive benzodithiophenes of the present invention, in order to induce or enhance liquid crystal phase behaviour.

Thus, another aspect of the invention relates to a reactive liquid crystal mixture comprising one or more reactive benzodithiophenes of the present invention, and optionally comprising one or more further reactive compounds, wherein at least one of the reactive benzodithiophenes and the further reactive compounds is mesogenic or liquid crystalline.

Particularly preferred are reactive mesogenic benzodithiophenes of the present invention, or mixtures comprising one or more reactive benzodithiophenes of the present invention, that exhibit a liquid crystal phase, especially a nematic and/or smectic liquid crystal phase.

Another aspect of invention relates to an anisotropic polymer film with charge transport properties obtainable from a reactive liquid crystal mixture as defined above that is aligned in its liquid crystal phase into macroscopically ordered orientation and polymerised or cross-linked to fix the oriented state.

Another aspect of the invention relates to a liquid crystal side chain polymer (SCLCP) obtained from a reactive liquid crystal material as defined above by polymerisation or polymeranaloguous reaction. Particularly preferred are SCLCPs obtained from one or more reactive benzodithiophenes or from a reactive mixture comprising one or more benzodithiophenes as described above.

Another aspect of the invention relates to an SCLCP obtained from one or more reactive benzodithiophenes or from a reactive liquid crystal mixture as defined above, by copolymerisation or polymeranaloguous reaction together with one or more additional mesogenic or non-mesogenic comonomers.

Side chain liquid crystal polymers or copolymers (SCLCPs), in which the semiconducting component is located as a pendant group, separated from a flexible backbone by an aliphatic spacer group, offer the possibility to obtain a highly ordered lamellar like morphology. This structure consists of closely packed conjugated aromatic mesogens, in which very close (typically <4 Å) pi—pi stacking can occur. This stacking allows intermolecular charge transport to occur more easily, leading to high charge carrier mobilities. SCLCPs are advantageous for specific applications as they can be readily synthesized before processing and then e.g. be processed from solution in an organic solvent. If SCLCPs are used in solutions, they can orient spontaneously when coated onto an appropriate surface and when at their mesophase temperature, which can result in large area, highly ordered domains.

The invention also relates to the use of reactive mesogenic benzodithiophenes of the present invention, or liquid crystal mixtures or polymers obtained thereof, as light-modulating component in liquid crystal displays, which may for example be switchable between two different states by an electric field, for components of liquid crystal displays, in particular optical retardation or compensation films, alignment layers or polarisers, or in other optical or electrooptical devices.

The invention also relates to a liquid crystal display, component of a liquid crystal display, in particular an optical retardation or compensation films, alignment layer or polariser, or an other optical or electrooptical device comprising reactive benzodithiophenes according to the present invention, or liquid crystal mixtures or polymer films obtained thereof.

The benzodithiophene groups in the compounds of the present invention are preferably linked to their neighbouring groups at the 2- and 6-position.

Especially preferred are compounds selected of formula I

P-Sp-X-T-R    I wherein
P is a polymerisable or reactive group,
Sp is a spacer group or a single bond,
X is a linkage group or a single bond,
R is H, halogen, CN, $NO_2$, an aliphatic, alicyclic or aromatic group with up to 40 C atoms that optionally comprises one or more hetero atoms and wherein one or more rings can be fused, or P-Sp-X—, and
T is a mesogenic group comprising one or more benzodithiophene groups that are substituted or unsubstituted.

R in formula I is preferably H, F, Cl or straight chain, branched or cyclic alkyl with 1 to 20 C-atoms, which is unsubstituted, mono- or polysubstituted by F, Cl, Br, I or CN, and wherein one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —$CY^1$=$CY^2$— or —C≡C— in such a manner that O and/or S atoms are not linked directly to one another, or an aryl or heteroaryl group, with $Y^1$ and $Y^2$ being independently of one another H, F, Cl or CN.

Particularly preferably R is optionally fluorinated alkyl or alkoxy with 1 to 15 C atoms.

Further preferred are compounds of formula I wherein R is P-Sp-X—.

T in formula I preferably comprises 1 or 2 benzodithiophene groups.

Particularly preferably T is selected of formula II

-$Z^1$-($A^1$-$Z^2$)$_m$-($T^1$-$Z^3$)$_n$-($A^2$-$Z^4$)$_o$-    II wherein
$A^1$ and $A^2$ are independently of each other an aryl, heteroaryl, or alicyclic group with up to 18 C atoms which is unsubstituted, mono- or polysubstituted with $R^1$, and $A^1$ may also denote $T^1$,
$Z^1$ to $Z^4$ are independently of each other —O—, —S—, —CO—, —COO—, —OCO—, —O—COO—, —CO—$NR^0$—, —$NR^0$—CO—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^0$—, —$CY^1$=$CY^2$—, —C≡C—, —CH=CH—COO—, —OCO—CH=CH— or a single bond,
$Y^1$ and $Y^2$ are independently of each other H, F, Cl or CN,
$T^1$ is a group consisting of 1 or 2 benzodithiophene units which are optionally substituted by $R^1$,
$R^1$ is H, halogen, CN, $NO_2$, SCN, $SF_5$, straight chain, branched or cyclic alkyl with 1 to 20 C-atoms, which is unsubstituted, mono- or polysubstituted by F, Cl, Br, I or CN, and wherein one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —$CY^1$=$CY^2$— or —C≡C— in such a manner that O and/or S atoms are not linked directly to one another, an aryl or heteroaryl group, or P-Sp-X,
$R^0$ and $R^{00}$ are independently of each other H or alkyl with 1 to 12 C-atoms,
m and o are independently of each other 0, 1, 2 or 3, and n is 1, 2 or 3

Particularly preferred groups T are those wherein $Z^1$, $A^1$, $Z^2$, $T^1$, $Z^3$, $A^2$ and $Z^4$ form a conjugated system. Therein $A^1$ and $A^2$ are preferably arylene or heteroarylene and $Z^1$, $Z^2$, $Z^3$ and $Z^4$ are preferably a single bond or a conjugated link such as —$CY^1$=$CY^2$— or —C≡C—.

Further preferred groups T are those wherein m and o are 0, further those wherein m and o are 1 or 2.

Further preferred groups T are those wherein $T^1$ is benzodithiophene that is optionally substituted with $R^1$ as defined above, furthermore those wherein n is 1 or 2 and $Z^2$ is a single bond or a conjugated link such as —$CY^1$=$CY^2$— or —C≡C—.

Particularly preferred groups T are those of the following formulae

| | |
|---|---|
| —$Z^1$—$T^1$—$Z^3$— | II1 |
| —$Z^1$—$A^1$—$Z^2$—$T^1$—$Z^3$— | II2 |
| —$Z^1$—$T^1$—$Z^3$—$T^1$—$Z^3$— | II3 |
| —$Z^1$—$A^1$—$Z^2$—$T^1$—$Z^3$—$A^2$—$Z^4$— | II4 |
| —$Z^1$—$A^1$—$Z^2$—$A^1$—$Z^2$—$T^1$—$Z^3$— | II5 |
| —$Z^1$—$A^1$—$Z^2$—$T^1$—$Z^3$—$T^1$—$Z^3$— | II6 |
| —$Z^1$—$T^1$—$Z^2$—$A^1$—$Z^2$—$T^1$—$Z^3$— | II7 |
| —$Z^1$—$A^1$—$Z^2$—$A^1$—$Z^2$—$T^1$—$Z^3$—$A^2$—$Z^4$— | II8 |
| —$Z^1$—$A^1$—$Z^2$—$A^1$—$Z^2$—$A^1$—$Z^2$—$T^2$—$Z^3$— | II9 |

| | |
|---|---|
| —Z¹—A¹—Z²—A¹—Z²—T¹—Z³—T²—Z³— | II10 |
| —Z¹—A¹—Z²—T¹—Z²—A¹—Z²—T²—Z³— | II11 |
| —Z¹—A¹—Z²—T¹—Z³—T¹—Z³—A²—Z⁴— | II12 |
| —Z¹—T¹—Z²—A¹—Z²—A¹—Z²—T²—Z³— | II13 |
| —Z¹—A¹—Z²—T¹—Z³—T¹—Z³—T¹—Z³— | II14 |
| —Z¹—T¹—Z²—A¹—Z²—T¹—Z³—T¹—Z³— | II15 |
| —Z¹—A¹—Z²—A¹—Z²—A¹—Z²—A¹—Z²—T¹—Z³— | II16 |
| —Z¹—A¹—Z²—A¹—Z²—A¹—Z²—T¹—Z³—A¹—Z⁴— | II17 |
| —Z¹—A¹—Z²—A¹—Z²—T¹—Z³—A²—Z⁴—A²—Z⁴— | II18 |
| —Z¹—A¹—Z²—A¹—Z²—A¹—Z²—T¹—Z³—T¹—Z³— | II19 |
| —Z¹—A¹—Z²—A¹—Z²—T¹—Z²—A¹—Z²—T¹—Z³— | II20 |
| —Z¹—A¹—Z²—A¹—Z²—T¹—Z²—T¹—Z³—T¹—Z³— | II21 |
| —Z¹—A¹—Z²—T¹—Z²—A¹—Z²—T¹—Z³—A²—Z⁴— | II22 |
| —Z¹—A¹—Z²—T¹—Z²—A¹—Z²—T¹—Z³—A²—Z⁴— | II23 |
| —Z¹—T¹—Z²—A¹—Z²—A¹—Z²—A¹—Z²—T¹—Z³— | II24 |
| —Z¹—A¹—Z²—A¹—Z²—T¹—Z³—T¹—Z³—T¹—Z³— | II25 |
| —Z¹—A¹—Z²—T¹—Z²—A¹—Z²—T¹—Z³—T¹—Z³— | II26 |
| —Z¹—A¹—Z²—T¹—Z²—T¹—Z²—A¹—Z²—T¹—Z³— | II27 |
| —Z¹—A¹—Z²—T¹—Z³—T¹—Z³—T¹—Z³—A²—Z⁴— | II28 |
| —Z¹—T¹—Z²—A¹—Z²—T¹—Z²—A¹—Z²—T¹—Z³— | II29 |
| —Z¹—T¹—Z²—A¹—Z²—A¹—Z²—T¹—Z³—T¹—Z³— | II30 | wherein $Z^1$, $Z^2$, $Z^3$, $Z^4$, $A^1$, $A^2$ and $T^1$ have in each case independently one of the meanings of formula II.

$T^1$ is preferably benzo[1,2-b:4,5-b']thiophene-2,6-diyl or [2,2']-bibenzo[1,2-b:4,5-b']thiophene-6,6'-diyl, all of which are optionally mono- or polysubstituted by halogen, CN, NO₂, straight chain, branched or cyclic alkyl with 1 to 20 C-atoms, which is unsubstituted, mono- or polysubstituted by F, Cl, Br, I or CN, and wherein one or more non-adjacent CH₂ groups are optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CY¹=CY²— or —C≡C— in such a manner that O and/or S atoms are not linked directly to one another, an aromatic or heteroaromatic group, or P-Sp-X.

$T^1$ is preferably selected from the following subformulae

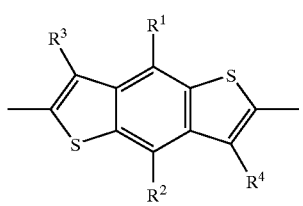

IIIa

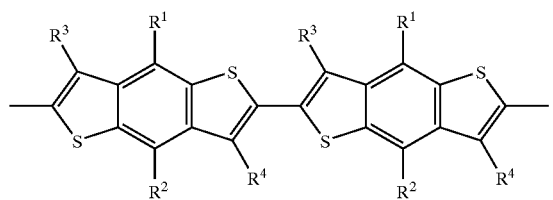

IIIb wherein $R^1$ to $R^4$ have independently of one another one of the meanings of $R^1$ in formula II, and are preferably H, halogen, methyl, ethyl, propyl, CO₂Me, CO₂Et, CN, COCH₃ or CHO.

$A^1$ and $A^2$ are preferably selected from 1,4-phenylene, 1,4-cyclohexa-1,3-diene, 1,4-cyclohexenylene in which, in addition, one or more CH groups are optioanlly replaced by N or one or two non-adjacent CH₂ groups are optionally replaced by O and/or S, thiophene-2,5-diyl, thienothiophene-2,5-diyl, dithienothiophene-2,6-diyl, 1,4-bicyclo-(2,2,2)-octylene, naphthalene-2,6-diyl, furan 2,5 diyl, and indane-2,5-diyl, wherein all these groups are unsubstituted, mono- or polysubstituted by L, with L being F, Cl, Br, CN, SCN, NO₂, SF₅ or an alkyl, alkoxy, alkylcarbonyl or alkoxycarbonyl group with 1 to 12 C atoms, wherein one or more H atoms are optionally replaced by F or Cl.

$A^1$ and $A^2$ are particularly preferably 1,4-phenylene that is substituted with 1, 2 or 3 groups L as defined above, or thiophene-2,5-diyl, which is optionally substituted with one or more groups L as defined above.

$Z^{1-4}$ are preferably selected from —O—, —S—, —OCH₂—, —CH₂O—, —SCH₂—, —CH₂S—, —CF₂O—, —OCF₂—, —CF₂S—, —SCF₂—, —CH₂CH₂—, —CF₂CH₂—, —CH₂CF₂—, —CF₂CF₂—, —CH=N—, —N=CH—, —N=N—, —CH=CR⁰—, —CY¹=CY²—, —C≡C— and a single bond, in particular from —CH=N—, —N=CH—, —N=N—, —CH=CR⁰—, —CY¹=CY²—, —C=C— and a single bond.

Particularly preferred are the following compounds

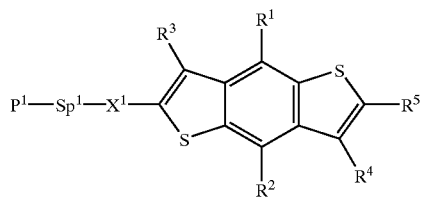

I1

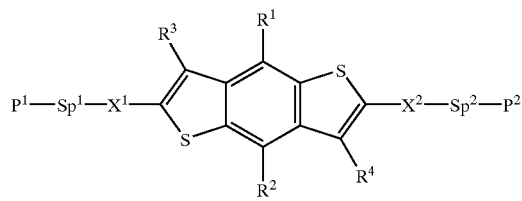

I2

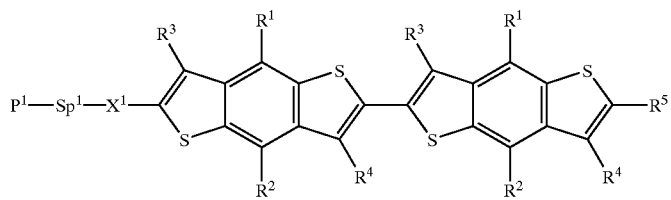
I3
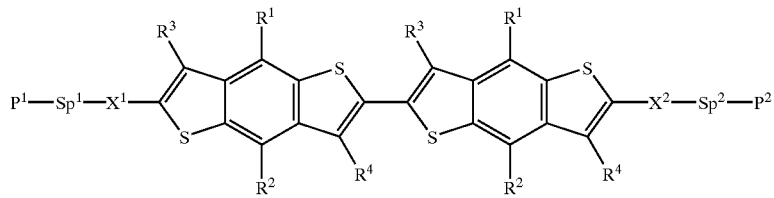
I4
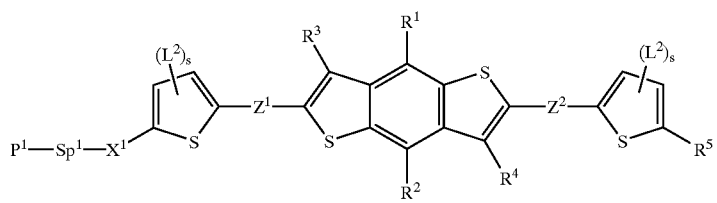
I5
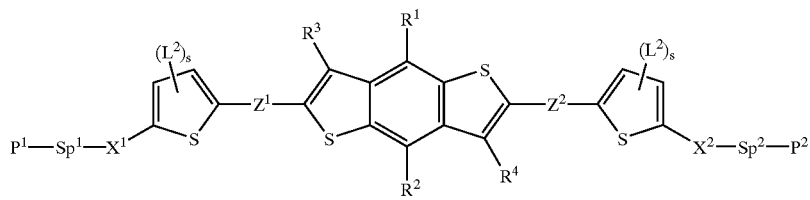
I6
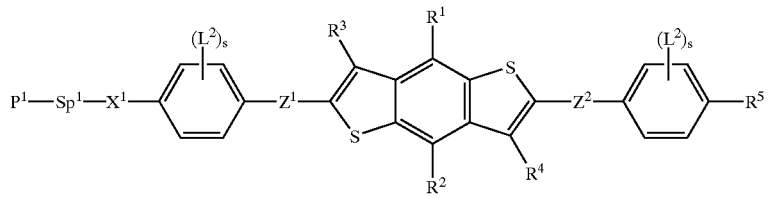
I7
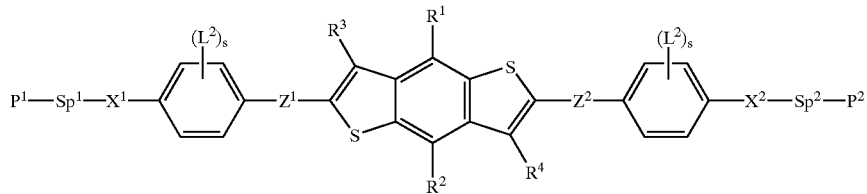
I8
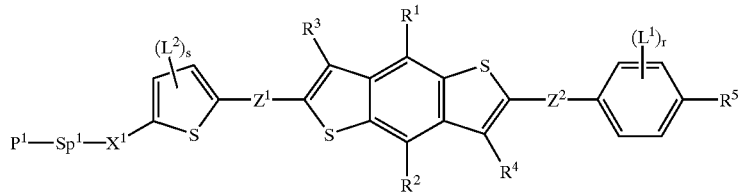
I9
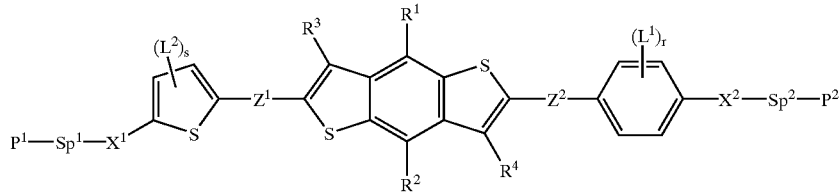
I10

-continued
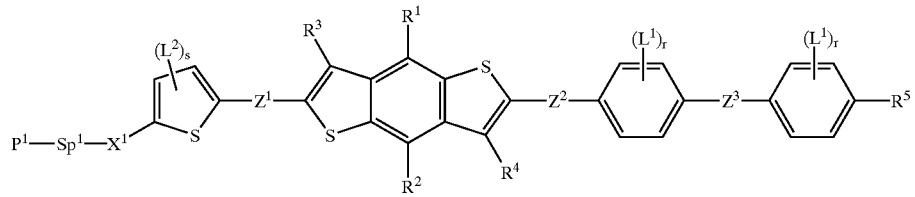
I11
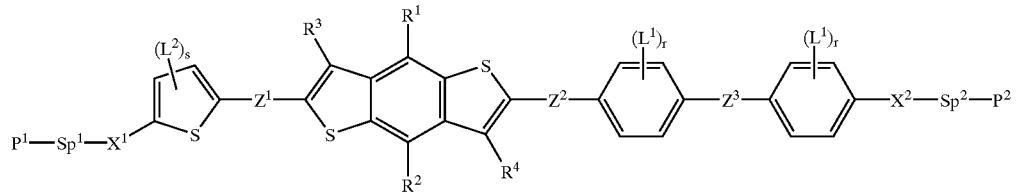
I12
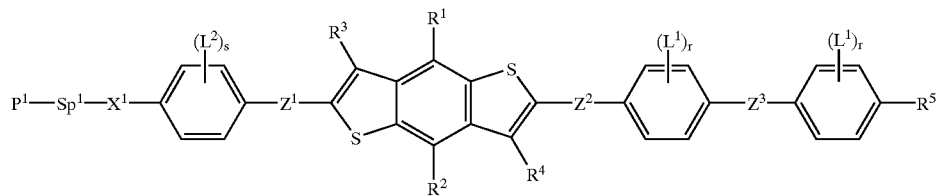
I13
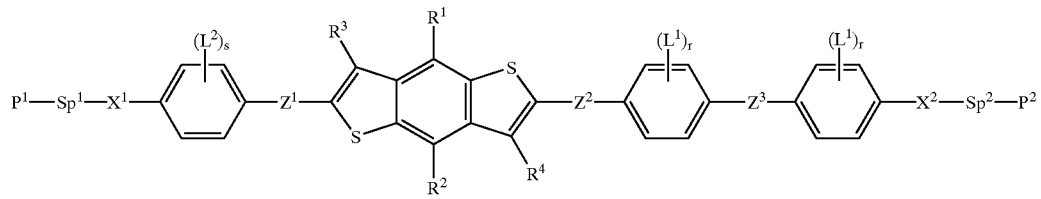
I14
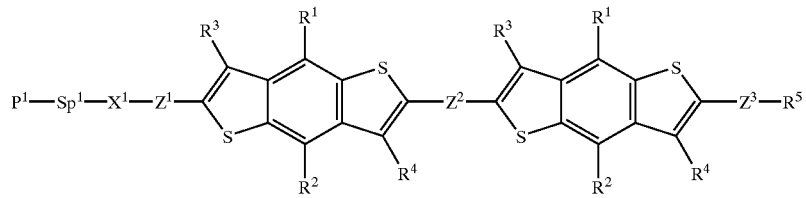
I15
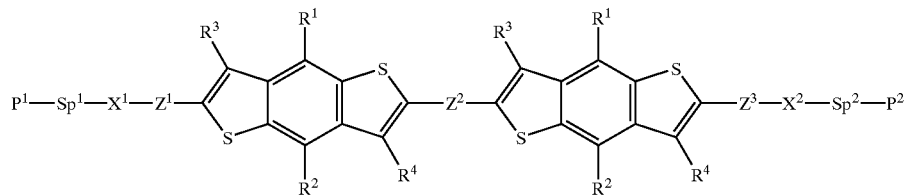
I16
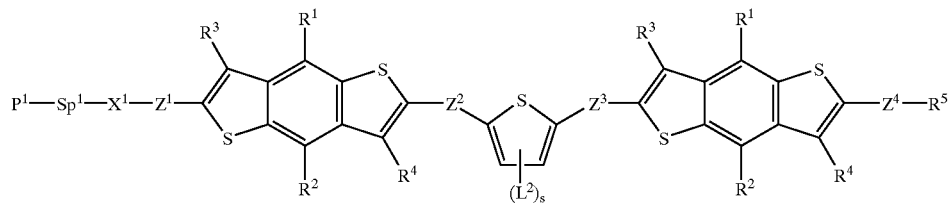
I17

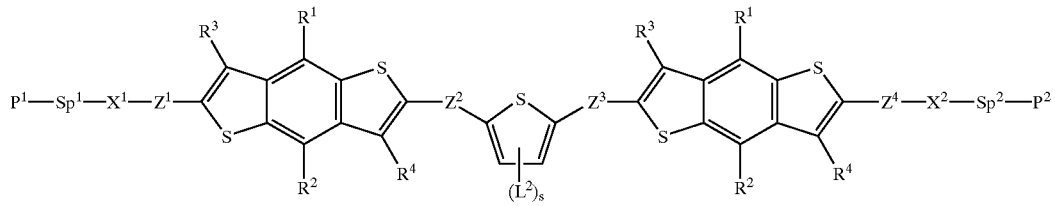

I18

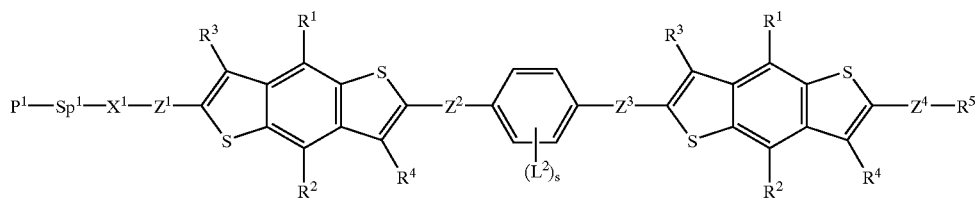

I19

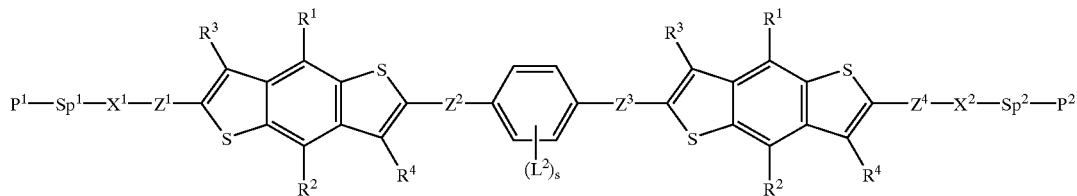

I20 wherein
$P^1$ and $P^2$ are identical or different groups P as defined in formula I,
$Sp^1$ and $Sp^2$ are identical or different groups Sp as defined in formula I,
$X^1$ and $X^2$ are identical or different groups X as defined in formula I,
$Z^1$ to $Z^4$ are as defined in formula II, and are preferably —CH=CH—, —CH=CF—, —CF=CH—, CH=CCl—, —CCl=CH—, —CF=CF—, —CCl=CCl—, —C≡C— or a single bond,
$R^1$ to $R^4$ have independently of one another the meaning of $R^1$ in formula II, and are preferably halogen or an optionally fluorinated alkyl group with 1 to 15 C atoms,
$R^5$ has one of the meanings of $R^1$ given in formula II, and is preferably halogen or an optionally fluorinated alkyl group with 1 to 15 C atoms,
$L^1$ has one of the meanings of L given above, and is preferably F, Cl or alkyl or alkoxy with 1 to 3 C-atoms that is optionally mono-, poly- or perfluorinated,
$L^2$ has one of the meanings of L given above, and is preferably alkyl with 1 to 12 C-atoms that is optionally mono-, poly- or perfluorinated,
r is 0, 1, 2, 3 or 4, and
s is 0, 1 or 2.

If in the above formulae a group $X^{1,2}$ is adjacent to a group $Z^{1-4}$, preferably at least one of $X^{1,2}$ and $Z^{1-4}$ is a single bond.

In the foregoing and the following, arylene and heteroarylene preferably denote a bivalent mono-, bi- or tricyclic aromatic or heteroaromatic group with up to 25 C atoms that optionally comprises fused rings and wherein the heteroaromatic groups contain at least one hetero atom, preferably selected from N, O and S, and which in each case is optionally substituted with one or more groups selected from H, CN, halogen and straight chain, branched or cyclic alkyl with 1 to 20 C-atoms, which is unsubstituted, mono- or poly-substituted by F, Cl, Br, I or CN, and in which one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another.

Very preferred arylene and heteroarylene groups are those having one of the preferred meanings of $A^1$ as given above and below.

Aryl and heteroaryl preferably denote a mono-, bi- or tricyclic aromatic or heteroaromatic group with up to 25 C atoms that optionally comprises fused rings and wherein the heteroaromatic groups contain at least one hetero atom, preferably selected from N, O and S, and which in each case is optionally substituted with one or more groups selected from H, CN, halogen and straight chain, branched or cyclic alkyl with 1 to 20 C-atoms, which is unsubstituted, mono- or poly-substituted by F, Cl, Br, I or CN, and in which one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH, — or —C≡C— in such a manner that O and/or S atoms are not linked directly to one another.

Especially preferred aryl and heteroaryl groups are phenyl in which, in addition, one or more CH groups are optionally replaced by N, naphthalene, thiophene, thienothiophene, dithienothiophene, alkyl fluorene and oxazole, all of which are unsubstituted, mono- or polysubstituted with L, wherein L is halogen or an alkyl, alkoxy, alkylcarbonyl or alkoxycarbonyl group with 1 to 12 C atoms, wherein one or more H atoms are optionally replaced by F or Cl.

Further preferred aryl and heteroaryl groups include five-membered heterocyclics like oxazole or isoxazole, N-substituted imidazole or pyrazole, thiazole or isothiazole, oxadiazole, N-substituted triazole, six-membered heterocyclics like pyridine, pyridazine, pyrimidine, pyrazine, triazine and tetrazine, heterocyclics with fused rings like benzoxazole, benzothiazole, benzimidazole, quinoline, isoquinoline, cinnoline, quinazoline, quinoxaline, phthalazine, benzothiadiazole, benzotriazole, benzotriazine, phenazine, phenanthridine, acridine, or condensed polycyclics like acenaphthene, phenanthrene, anthracene, fluoranthene, pyrene, perylene, rubrene, chrysene, naphthacene, coronene or triphenylene, all of which are unsubstituted, mono- or polysubstituted with L as defined above.

—$CY^1$=$CY^2$— is preferably —CH=CH—, —CH=CF—, —CF=CH—, —CF=CF—, —CH=C(CN)— or —C(CN)=CH—.

If one of $R^1$ to $R^5$ is an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

Halogen is preferably F or Cl.

Hetero atoms are preferably selected from N, O and S.

The polymerisable or reactive group P is preferably selected from $CH_2$=$CW^1$-COO—,

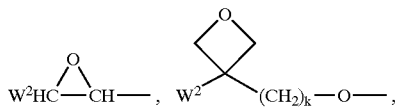

$CH_2$=$CW^2$-$(O)_{k1}$—, $CH_3$—CH=CH—O—, $(CH_2$=$CH)_2$CH—OCO—, $(CH_2$=CH—$CH_2)_2$CH—OCO—, $(CH_2$=$CH)_2$CH—O—, $(CH_2$=CH—$CH_2)_2$N—, HO—$CW^2W^3$-, HS—$CW^2W^3$-, $HW^2$N—, HO—$CW^2W^3$-NH—, $CH_2$=$CW^1$-CO—NH—, $CH_2$=CH—$(COO)_{k1}$-Phe-$(O)_{k2}$—, Phe-CH=CH—, HOOC—, OCN—, and $W^4W^5W^6$Si—, with $W^1$ being H, Cl, CN, phenyl or alkyl with 1 to 5 C-atoms, in particular H, Cl or $CH_3$, $W^2$ and $W^3$ being independently of each other H or alkyl with 1 to 5 C-atoms, in particular methyl, ethyl or n-propyl, $W^4$, $W^5$ and $W^6$ being independently of each other Cl, oxaalkyl or oxacarbonylalkyl with 1 to 5 C-atoms, Phe being 1,4-phenylene and $k_1$ and $k_2$ being independently of each other 0 or 1.

Especially preferred groups P are $CH_2$=CH—COO—, $CH_2$=C($CH_3$)—COO—, $CH_2$=CH—, $CH_2$=CH—O—, $(CH_2$=$CH)_2$CH—OCO—, $(CH_2$=$CH)_2$CH—O—, and

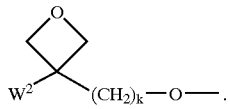

Very preferred are acrylate and oxetane groups. Oxetanes produce less shrinkage upon polymerisation (cross-linking), which results in less stress development within films, leading to higher retention of ordering and fewer defects. Oxetane cross-linking also requires cationic initiator, which unlike free radical initiator is inert to oxygen.

As for the spacer group Sp all groups can be used that are known for this purpose to those skilled in the art, and is preferably linear or branched alkylene group having 1 to 20 C atoms, in particular 1 to 12 C atoms, in which, in addition, one or more non-adjacent $CH_2$ groups may be replaced by —O—, —S—, —NH—, —N($CH_3$)—, —CO—, —O—CO—, —S—CO—, —O—COO—, —CO—S—, —CO—O—, —CH(halogen)-, —C(halogen)$_2$, —CH(CN)—, —CH=CH— or —C≡C—, or a siloxane group.

Typical spacer groups are for example —$(CH_2)_p$—, —$(CH_2CH_2O)_r$—$CH_2CH_2$—, —$CH_2CH_2$—S—$CH_2CH_2$— or —$CH_2CH_2$—NH—$CH_2CH_2$— or —$(SiR^0R^{00}$—$O)_p$—, with p being an integer from 2 to 12, r being an integer from 1 to 3 and $R^0$ and $R^{00}$ having the meanings given in formula I.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyl-iminoethylene, 1-methylalkylene, ethenylene, propenylene and butenylene for example.

The linkage group X is preferably —O—, —S—, —$OCH_2$—, —$CH_2O$—, —CO—, —COO—, —OCO—, —OCO—O—, —CO—$NR^0$—, —$NR^0$—CO—, —$OCH_2$—, —$CH_2O$—, —$SCH_2$—, —$CH_2S$—, —CH=CH—COO—, —OOC—CH=CH—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^0$—, —$CY^1$=$CY^2$—, —C≡C— or a single bond, with $R^0$, $Y^1$ and $Y^2$ having the meanings given above.

In a preferred embodiment, the linkage group X is an unsaturated group that is capable of forming a conjugated system, such as —CH=N—, —N=CH—, —N=N—, —CH=$CR^0$—, —$CY^1$=$CY^2$—, —C≡C—, or a single bond.

Further preferred are compounds with one or two groups P-Sp-X wherein Sp and/or X is a single bond.

In case of compounds with two or more groups P-Sp-X, each of the groups P, the groups Sp, and the groups X can be identical or different.

SCLCPs obtained from the inventive compounds or mixtures by polymerisation or copolymerisation have a backbone that is formed by the polymerisable group P in formula I.

The compounds of formula I can be synthesized according to or in analogy to methods that are known to the skilled in the art and are reported in the literature. Furthermore, they can be prepared according to or in analogy to the following reaction schemes.

As shown in Scheme 1, fused benzodithiophene ring system 1 and its dimer 2 can be prepared as described e.g. in Katz et al., *J. Mater. Chem.* 1997, 7(3), 369–76, or Yoshida et al., *J. Org. Chem.* 1994, 59, 3077.

Scheme 1

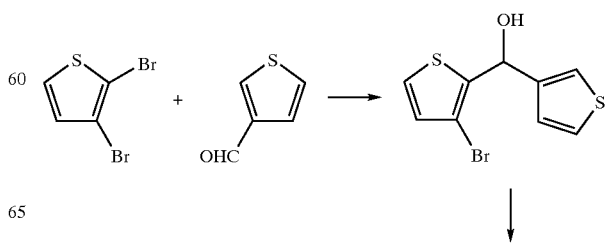

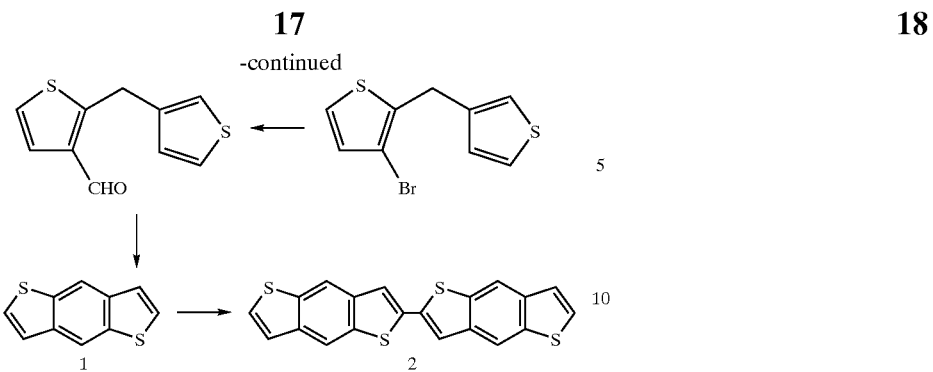

As shown in scheme 2, compound 1 can be lithiated and reacted with express iodine to give di-iododerivative 3, as described e.g. in Yoshida et al., *J. Org. Chem.* 1994, 59, 3077, and further reacted with acetylene compounds using the Sonogashira reaction to give compounds of type 5.

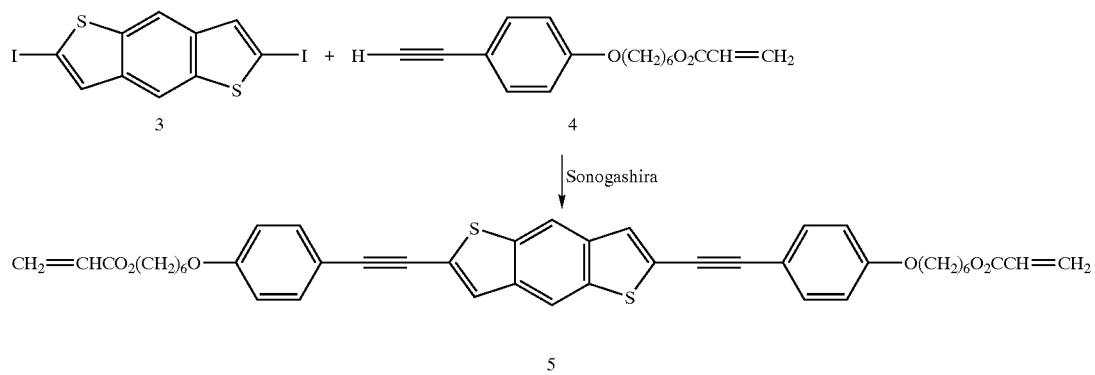

As shown in Scheme 3, compound 3 can be cross-coupled with boronic acids according to the Suzuki reaction to give compounds of type 7.

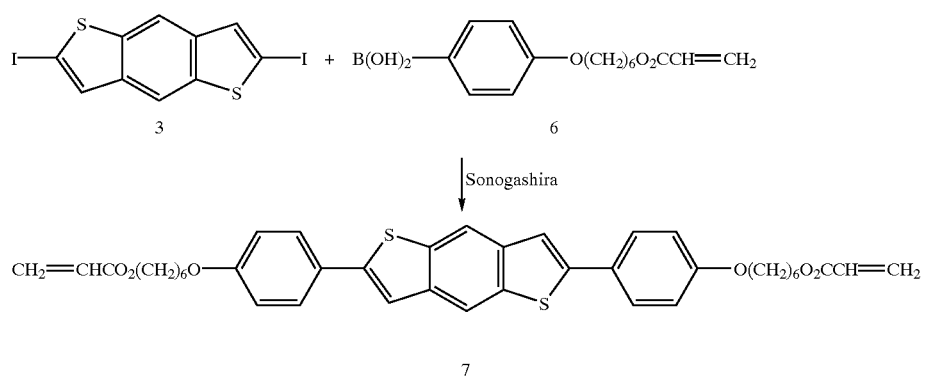

As shown in Scheme 4, reaction with one equivalent of boronic acid and Suzuki conditions followed by isolation gives compound 8. Reaction of an acetylene moiety gives an unsymmetrical compound of type 9.

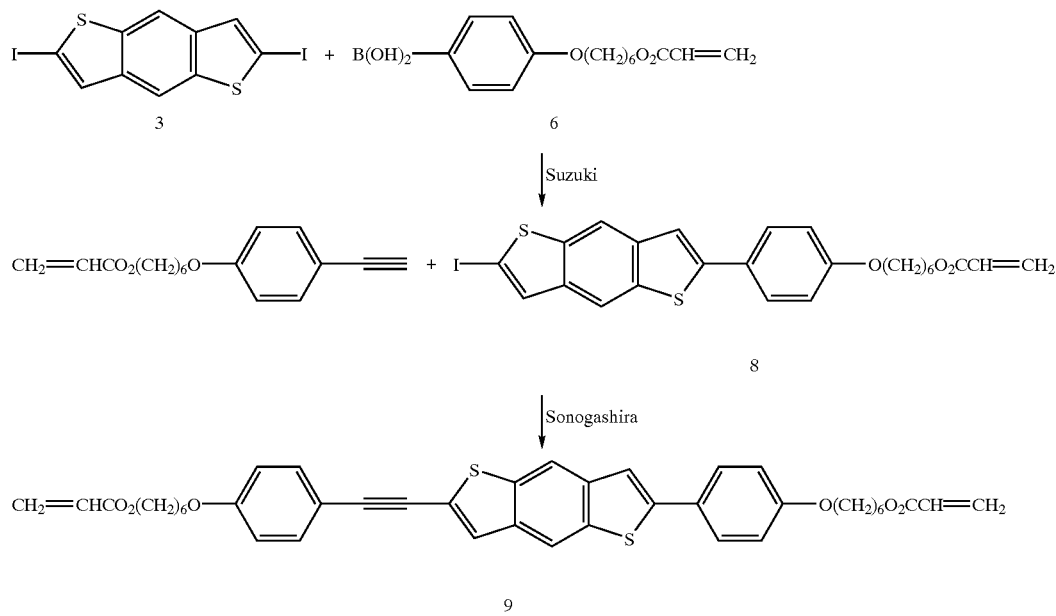

Scheme 4

As shown in Scheme 5, compound 10 formed from a Sonogashira cross-coupling can be reacted with a boronic acid ester to give compounds of type 12.

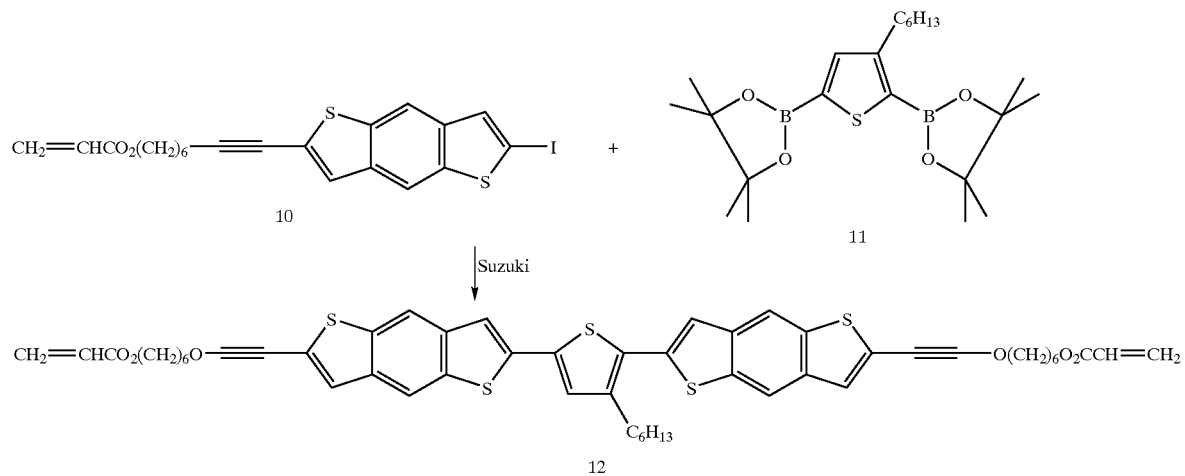

Scheme 5

In the compounds shown in Scheme 1–5 above, the central benzene ring of the benzodithiophene group can be easily substituted with alkyl or alkoxy groups, as described e.g. in Beimling et al., *Chem. Ber.* 1986, 119(10), 3198.

A preferred embodiment of the present invention relates to reactive benzodithiophenes, in particular those of formula I, that are mesogenic or liquid crystalline. These materials are particularly useful as semiconductors or charge transport materials, as they can be aligned into uniform highly ordered orientation in their liquid crystal phase by known techniques, thus exhibiting a higher degree of order that leads to particularly high charge carrier mobility. The highly ordered liquid crystal state can be fixed by in situ polymerisation or crosslinking via the groups P to yield polymer films with high charge carrier mobility and high-thermal, mechanical and chemical stability.

It is also possible to copolymerise the benzodithiophenes according to the present invention with other polymerisable mesogenic or liquid crystal monomers that are known from prior art, in order to induce or enhance liquid crystal phase behaviour.

Thus, another aspect of the invention relates to a polymerisable liquid crystal material comprising one or more polymerisable benzodithiophenes of the present invention as described above and below comprising at least one polymerisable group, and optionally comprising one or more further polymerisable compounds, wherein at least one of the polymerisable benzodithiophenes of the present invention and/or the further polymerisable compounds is mesogenic or liquid crystalline.

Particularly preferred are liquid crystal materials having a nematic and/or smectic phase. For FET applications smectic materials are especially preferred. For OLED applications nematic or smectic materials are especially preferred.

Another aspect of the invention relates to an anisotropic polymer film with charge transport properties obtainable from a polymerisable liquid crystal material as defined above that is aligned in its liquid crystal phase into macroscopically uniform orientation and polymerised or crosslinked to fix the oriented state.

Polymerisation is preferably carried out by in-situ polymerisation of a coated layer of the material, preferably during fabrication of the electronic or optical device comprising the inventive semiconductor material. In case of liquid crystal materials, these are preferably aligned in their liquid crystal state into homeotropic orientation prior to polymerisation, where the conjugated pi-electron systems are orthogonal to the direction of charge transport. This ensures that the intermolecular distances are minimised and hence then energy required to transport charge between molecules is minimised. The molecules are then polymerised or crosslinked to fix the uniform orientation of the liquid crystal state. Alignment and curing are carried out in the liquid crystal phase or mesophase of the material. This technique is known in the art and is generally described for example in D. J. Broer, et al., Angew. Makromol. Chem. 183, (1990), 45–66

Alignment of the liquid crystal material can be achieved for example by treatment of the substrate onto which the material is coated, by shearing the material during or after coating, by application of a magnetic or electric field to the coated material, or by the addition of surface-active compounds to the liquid crystal material. Reviews of alignment techniques are given for example by I. Sage in "Thermotropic Liquid Crystals", edited by G. W. Gray, John Wiley & Sons, 1987, pages 75–77, and by T. Uchida and H. Seki in "Liquid Crystals—Applications and Uses Vol. 3", edited by B. Bahadur, World Scientific Publishing, Singapore 1992, pages 1–63. A review of alignment materials and techniques is given by J. Cognard, Mol. Cryst. Liq. Cryst. 78, Supplement 1 (1981), pages 1–77.

Polymerisation takes place by exposure to heat or actinic radiation. Actinic radiation means irradiation with light, like UV light, IR light or visible light, irradiation with X-rays or gamma rays or irradiation with high energy particles, such as ions or electrons. Preferably polymerisation is carried out by UV irradiation at a non-absorbing wavelength. As a source for actinic radiation for example a single UV lamp or a set of UV lamps can be used. When using a high lamp power the curing time can be reduced. Another possible source for actinic radiation is a laser, like e.g. a UV laser, an IR laser or a visible laser.

Polymerisation is preferably carried out in the presence of an initiator absorbing at the wavelength of the actinic radiation. For example, when polymerising by means of UV light, a photoinitiator can be used that decomposes under UV irradiation to produce free radicals or ions that start the polymerisation reaction. When curing polymerisable materials with acrylate or methacrylate groups, preferably a radical photoinitiator is used, when curing polymerisable materials with vinyl, epoxide and oxetane groups, preferably a cationic photoinitiator is used. It is also possible to use a polymerisation initiator that decomposes when heated to produce free radicals or ions that start the polymerisation. As a photoinitiator for radical polymerisation for example the commercially available Irgacure 651, Irgacure 184, Darocure 1173 or Darocure 4205 (all from Ciba Geigy AG) can be used, whereas in case of cationic photopolymerisation the commercially available UVI 6974 (Union Carbide) can be used.

The polymerisable material can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

Polymerisable benzodithiophenes comprising one or more groups P-Sp-X can also be copolymerised with polymerisable mesogenic compounds to induce, or, in case of mesogenic materials of formula I, enhance liquid crystal phase behaviour. Polymerisable mesogenic compounds that are suitable as comonomers are known in prior art and disclosed for example in WO 93/22397; EP 0,261,712; DE 195,04,224; WO 95/22586 and WO 97/00600.

SCLCPs can be prepared from the polymerisable compounds or mixtures according to the invention by the methods described above, or by conventional polymerisation techniques which are known to those skilled in the art, including for example radicalic, cationic or anionic polymerisation from unsaturated functionality radicalic, polyaddition or polycondensation. Polymerisation can be carried out for example as polymerisation in solution, without the need of coating and prior alignment, or polymerisation in situ.

It is also possible to form SCLCPs by grafting compounds according to the invention with a suitable reactive group, or mixtures thereof, to presynthesized isotropic or anisotropic polymer backbones in a polymeranaloguous reaction. For example, compounds with a terminal hydroxy group can be attached to polymer backbones with lateral carboxylic acid or ester groups, compounds with terminal isocyanate groups can be added to backbones with free hydroxy groups, compounds with terminal vinyl or vinyloxy groups can be added e.g. to polysiloxane backbones with Si—H groups.

It is also possible to form SCLCPs by copolymerisation or polymeranaloguous reaction from the inventive compounds together with conventional mesogenic or non mesogenic comonomers. Suitable comonomers are known to those skilled in the art. In principle it is possible to use all conventional comonomers known in the art that carry a reactive or polymerisable group capable of undergoing the desired polymer-forming reaction, like for example a polymerisable or reactive group P as defined above. Typical mesogenic comonomers are for example those mentioned in WO 93/22397; EP 0,261,712; DE 195,04,224; WO 95/22586 and WO 97/00600. Typical non mesogenic comonomers are for example alkyl mono- or diacrylates or alkyl mono- or dimethacrylates with alkyl groups of 1 to 20 C atoms, like methyl acrylate or methyl methacrylate, trimethylpropane trimethacrylate or pentaerythritol tetraacrylate.

For example, if a device is made from a polymerisable liquid crystal material by polymerisation in situ, the liquid crystal material preferably comprises one or more compounds of formula I and its preferred subformulae having one or more groups P. If a liquid crystal polymer is prepared first, for example by polymerisation in solution, and the isolated polymer is used to make the device, the polymer is preferably made from a liquid crystal material comprising one or more compounds of formula I and its preferred subformulae having one group P.

The materials of the present invention are useful as optical, electronic and semiconductor materials, in particular as charge transport materials in field effect transistors (FETs) e.g. as components of integrated circuitry, ID tags or TFT applications. Alternatively, they may be used in organic light emitting diodes (OLEDs) in electroluminescent display applications or as backlight of e.g. liquid crystal displays, as photovoltaics or sensor materials, for electrophotographic recording, and for other semiconductor applications.

Especially the oligomers and polymers according to the invention show advantageous solubility properties which allow production processes using solutions of these compounds. Thus films, including layers and coatings, may be generated by low cost production techniques e.g. spin coating. Suitable solvents or solvent mixtures comprise alkanes and/or aromatics, especially their fluorinated derivatives.

The materials of the present invention are useful as optical, electronic and semiconductor materials, in particular as charge transport materials in field effect transistors (FETs), as photovoltaics or sensor materials, for electrophotographic recording, and for other semiconductor applications. Such FETs, where an organic semiconductive material is arranged as a film between a gate-dielectric and a drain and a source electrode, are generally known e.g. from U.S. Pat. No. 5,892,244, WO 00/79617, U.S. Pat. No. 5,998,804, and from the references cited in the background and prior art chapter and listed below. Due to the advantages, like low cost production using the solubility properties of the compounds according to the invention and thus the processibility of large surfaces, preferred applications of these FETs are such as integrated circuitry, TFT-displays and security applications.

In security applications, field effect transistors and other devices with semiconductive materials, like transistors or diodes, may be used for ID tags or security markings to authenticate and prevent counterfeiting of documents of value like banknotes, credit cards or ID cards, national ID documents, licenses or any product with money value, like stamps, tickets, shares, cheques etc.

Alternatively, the materials according to the invention may be used in organic light emitting devices or diodes (OLEDs), e.g. in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see e. g. Meerhoiz, Synthetic Materials, 111–112, 2000, 31–34, Alcala, J. Appl. Phys., 88, 2000, 7124–7128 and the literature cited therein.

According to another use, the inventive compounds, materials or films, especially those which show photoluminescent properties, may be employed as materials of light sources, e.g. of display devices such as described in EP 0 889 350 A1 or by C. Weder et al., Science, 279,1998, 835–837.

The materials of the present invention are also useful for the preparation of optical films with anisotropic properties, like for example polarizers, optical retardation films, compensators, colour filters, polarization beam splitters, or polarization filters, which can be used for example as components of liquid crystal displays. Furthermore, they can be used as coatings e.g. for decorative or security use, as adhesives, or for the preparation of liquid crystal pigments.

A further aspect of the invention relates to both the oxidised and reduced form of the compounds and materials according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g. $I_2$, $Cl_2$, $Br_2$, ICl, $ICl_3$, IBr and IF), Lewis acids (e.g. $PF_5$, $AsF_5$, $SbF_5$, $BF_3$, $BCl_3$, $SbCl_5$, $BBr_3$ and $SO_3$), protonic acids, organic acids, or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g. $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g. $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns ot tracts in electronic applications such as printed circuit boards and condensers.

What is claimed is:

1. A reactive mesogenic benzodithiophene comprising a central mesogenic core comprising one or more benzo[1,2-b:4,5-b']dithiophene groups linked to one or more reactive groups.

2. The reactive mesogenic benzodithiophene according to claim 1, further comprising unsaturated organic groups that form a conjugated system together with said benzo[1,2-b:4, 5-b']dithiophene groups.

3. The reactive mesogenic benzodithiophene according to claim 2, wherein said mesogenic core is linked via a spacer group to said reactive groups.

4. The reactive mesogenic benzodithiophene according to claim 1, wherein said mesogenic core is linked via a spacer group to said reactive groups.

5. The reactive mesogenic benzodithiophene according to claim 1, having formula I P-Sp-X-T-R     I wherein
P is a polymerisable or reactive group,
Sp is a spacer group or a single bond,
X is a linkage group or a single bond,
R is H, halogen, CN, NO$_2$, an aliphatic, alicyclic or aromatic group with up to 40 C atoms that optionally comprises one or more hetero atoms and wherein one or more rings can be fused, or is P-Sp-X, and
T is a mesogenic group comprising one or more benzo[1,2-b:4,5-b']dithiophene groups that are substituted or unsubstituted.

6. The reactive mesogenic benzodithiophene according to claim 5, wherein said Sp is —(CH$_2$)$_p$—, —(CH$_2$CH$_2$O)$_r$—CH$_2$CH$_2$—, —CH$_2$CH$_2$—S—CH$_2$CH$_2$— or —CH$_2$CH$_2$—NH—CH$_2$CH$_2$— or —(SiR$^0$R$^{00}$—O)$_p$—, with p being an integer from 2 to 12, r being an integer from 1 to 3 and R$^0$ and R$^{00}$ are independently of each other H or alkyl with 1 to 12 C-atoms.

7. The reactive mesogenic benzodithiophene according to claim 5, wherein said linkage group is —O—, —S—, —OCH$_2$—, —CH$_2$O—, —CO—, —COO—, —OCO—, —OCO—O—, —CO—NR$^0$—, —NR$^0$—CO—, —OCH$_2$—, —CH$_2$O—, —SCH$_2$—, —CH$_2$S—, —CH═CH—COO—, —OOC—CH═CH—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH═N—, —N═CH—, —N═N—, —CH═CR$^0$—, —CY$^1$═CY$^2$—, —C≡C— or a single bond, and wherein R$^0$ is H or alkyl with 1 to 12 C-atoms, Y$^1$ is H, F, Cl or CN, and Y$^2$ is H, F, Cl or CN.

8. The reactive mesogenic benzodithiophene according to claim 5, wherein T is selected from formula II -Z$^1$-(A$^1$-Z$^2$)$_m$-(T$^1$-Z$^3$)$_n$-(A$^2$-Z$^4$)$_o$-     II wherein
A$^1$ and A$^2$ are independently of each other an aromatic, heteroaromatic or alicyclic group with up to 18 C atoms which is unsubstituted, mono- or polysubstituted with R$^1$, and A$^1$ may also denote T$^1$,
Z$^1$ to Z$^4$ are independently of each other —O—, —S—, —CO—, —COO—, —OCO—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH═N—, —N═CH—, —N═N—, —CH═CR$^0$—, —CY$^1$═CY$^2$—, —C≡C—, —CH═CH—COO—, —OCO—CH═CH— or a single bond,
Y$^1$ and Y$^2$ are independently of each other H, F, Cl or CN,
T$^1$ is a group consisting of 1 or 2 benzo[1,2-b:4,5-b'] dithiophene units which are optionally substituted by R$^1$, R$^1$ is H, halogen, CN, NO$_2$, straight chain, branched or cyclic alkyl with 1 to 20 C-atoms, which is unsubstituted, mono- or polysubstituted by F, Cl, Br, I or CN, and wherein one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CY$^1$═CY$^2$— or —C≡C— in such a manner that O and/or S atoms are not linked directly to one another, an aromatic or heteroaromatic group, or is P-Sp-X,
R$^0$ and R$^{00}$ are independently of each other H or alkyl with 1 to 12 C-atoms,
m and o are independently of each other 0, 1, 2 or 3, and
n is 1, 2 or 3.

9. A reactive mesogenic benzodithiophene according to claim 8, wherein said aromatic or heteroaromatic groups are selected from mono-, bi- or tricyclic aromatic or heteroaromatic groups with up to 25 C atoms that optionally comprise fused rings and wherein the heteroaromatic groups contain at least one hetero atom selected from N, O and S, and which in each case is optionally substituted with one or more groups selected from H, CN, halogen and straight chain, branched or cyclic alkyl with 1 to 20 C-atoms, which is unsubstituted, mono- or poly-substituted by F, Cl, Br, I or CN, and in which one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH═CH, — or —C≡C— in such a manner that O and/or S atoms are not linked directly to one another.

10. The reactive mesogenic benzodithiophene according to claim 8, wherein at least one of said benzo[1,2-b:4,5-b'] diothiophene units of T$^1$ is substituted by R$^1$.

11. A reactive mesogenic benzodithiophene according to claim 10, wherein said aromatic or heteroaromatic groups are selected from mono-, bi- or tricyclic aromatic or heteroaromatic groups with up to 25 C atoms that optionally comprise fused rings and wherein the heteroaromatic groups contain at least one hetero atom selected from N, O and S, and which in each case is optionally substituted with one or more groups selected from H, CN, halogen and straight chain, branched or cyclic alkyl with 1 to 20 C-atoms, which is unsubstituted, mono- or poly-substituted by F, Cl, Br, I or CN, and in which one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH═CH, — or —C≡C— in such a manner that O and/or S atoms are not linked directly to one another.

12. The reactive mesogenic benzodithiophene according to claim 8, wherein T$^1$ is selected from the following subformulae IIIa

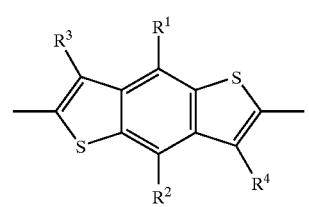

-continued

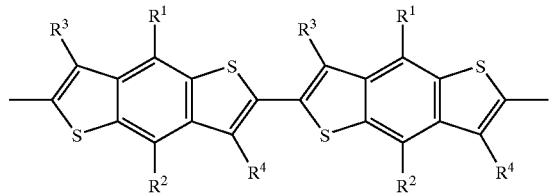

IIIb wherein R¹ to R⁴ are independently of one another H, halogen, CN, NO₂, straight chain, branched or cyclic alkyl with 1 to 20 C-atoms, which is unsubstituted, mono- or polysubstituted by F, Cl, Br, I or CN, and wherein one or more non-adjacent CH₂ groups are optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CY¹=CY²— or —C≡C— in such a manner that O and/or S atoms are not linked directly to one another, an aromatic or heteroaromatic group, or P-Sp-X.

13. A reactive mesogenic benzodithiophene according to claim 12, wherein said aromatic or heteroaromatic groups are selected from mono-, bi- or tricyclic aromatic or heteroaromatic groups with up to 25 C atoms that optionally comprise fused rings and wherein the heteroaromatic groups contain at least one hetero atom selected from N, O and S, and which in each case is optionally substituted with one or more groups selected from H, CN, halogen and straight chain, branched or cyclic alkyl with 1 to 20 C-atoms, which is unsubstituted, mono- or poly-substituted by F, Cl, Br, I or CN, and in which one or more non-adjacent CH₂ groups are optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH, — or —C≡C— in such a manner that O and/or S atoms are not linked directly to one another.

14. The reactive mesogenic benzodithiophene according to claim 8, wherein A¹ and A² are independently of each other 1,4-phenylene, 1,4-cyclohexa-1,3-diene, or 1,4-cyclohexenylene, in which, in addition, one or more CH groups are optionally replaced by N or one or two non-adjacent CH₂ groups are optionally replaced by O and/or S, thiophene-2,5-diyl, thienothiophene-2,5-diyl, dithienothiophene-2,6-diyl, 1,4-bicyclo-(2,2,2)-octylene, naphthalene-2,6-diyl, furan 2,5 diyl, or indane-2,5-diyl, in each case being unsubstituted or, mono- or polysubstituted by L, with L being F, Cl, Br, CN, SCN, NO₂, SF₅ or an alkyl, alkoxy, alkylcarbonyl or alkoxycarbonyl group with 1 to 12 C atoms, wherein one or more H atoms are optionally replaced by F or Cl.

15. A reactive mesogenic benzodithiophene according to claim 14, wherein said aromatic or heteroaromatic groups are selected from mono, bi- or tricyclic aromatic or heteroaromatic groups with up to 25 C atoms that optionally comprise fused rings and wherein the heteroaromatic groups contain at least one hetero atom selected from N, O and S, and which in each case is optionally substituted with one or more groups selected from H, CN, halogen and straight chain, branched or cyclic alkyl with 1 to 20 C-atoms, which is unsubstituted, mono- or poly-substituted by F, Cl, Br, I or CN, and in which one or more non-adjacent CH₂ groups are optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH, — or —C≡C— in such a manner that O and/or S atoms are not linked directly to one another.

16. The reactive mesogenic benzodithiophene according to claim 5, wherein T is selected from the following formulae

| | |
|---|---|
| —Z¹—T¹—Z³— | II1 |
| —Z¹—A¹—Z²—T¹—Z³— | II2 |
| —Z¹—T¹—Z³—T¹—Z³— | II3 |
| —Z¹—A¹—Z²—T¹—Z³—A²—Z⁴— | II4 |
| —Z¹—A¹—Z²—A¹—Z²—T¹—Z³— | II5 |
| —Z¹—A¹—Z²—T¹—Z³—T¹—Z³— | II6 |
| —Z¹—T¹—Z²—A¹—Z²—T¹—Z³— | II7 |
| —Z¹—A¹—Z²—A¹—Z²—T¹—Z³—A²—Z⁴— | II8 |
| —Z¹—A¹—Z²—A¹—Z²—A¹—Z²—T¹—Z³— | II9 |
| —Z¹—A¹—Z²—A¹—Z²—T¹—Z³—T¹—Z³— | II10 |
| —Z¹—A¹—Z²—T¹—Z²—A¹—Z²—T¹—Z³— | II11 |
| —Z¹—A¹—Z²—T¹—Z³—T¹—Z³—A²—Z⁴— | II12 |
| —Z¹—T¹—Z²—A¹—Z²—A¹—Z²—T¹—Z³— | II13 |
| —Z¹—A¹—Z²—A¹—Z²—T¹—Z³—T¹—Z³— | II14 |
| —Z¹—T¹—Z²—A¹—Z²—T¹—Z³—T¹—Z³— | II15 |
| —Z¹—A¹—Z²—A¹—Z²—A¹—Z²—A¹—Z²—T¹—Z³— | II16 |
| —Z¹—A¹—Z²—A¹—Z²—A¹—Z²—T¹—Z³—A¹—Z⁴— | II17 |
| —Z¹—A¹—Z²—A¹—Z²—T¹—Z³—A²—Z⁴—A²—Z⁴— | II18 |
| —Z¹—A¹—Z²—A¹—Z²—A¹—Z²—T¹—Z³—T¹—Z³— | II19 |
| —Z¹—A¹—Z²—A¹—Z²—T¹—Z²—A¹—Z²—T¹—Z³— | II20 |
| —Z¹—A¹—Z²—T¹—Z²—A¹—Z²—A¹—Z²—T¹—Z³— | II21 |
| —Z¹—A¹—Z²—A¹—Z²—T¹—Z³—T¹—Z³—A²—Z⁴— | II22 |
| —Z¹—A¹—Z²—T¹—Z²—A¹—Z²—T¹—Z³—A²—Z⁴— | II23 |
| —Z¹—T¹—Z²—A¹—Z²—A¹—Z²—A¹—Z²—T¹—Z³— | II24 |
| —Z¹—A¹—Z²—A¹—Z²—T¹—Z³—T¹—Z³—T¹—Z³— | II25 |
| —Z¹—A¹—Z²—T¹—Z²—A¹—Z²—T¹—Z³—T¹—Z³— | II26 |
| —Z¹—A¹—Z²—T¹—Z²—T¹—Z²—A¹—Z²—T¹—Z³— | II27 |
| —Z¹—A¹—Z²—T¹—Z³—T¹—Z³—T¹—Z³—A²—Z⁴— | II28 |
| —Z¹—T¹—Z²—A¹—Z²—T¹—Z²—A¹—Z²—T¹—Z³— | II29 |
| —Z¹—T¹—Z²—A¹—Z²—A¹—Z²—T¹—Z³—T¹—Z³— | II30 | wherein
A¹ and A² are independently of each other an aromatic, heteroaromatic or alicyclic group with up to 18 C atoms which is unsubstituted, mono- or polysubstituted with R¹, and A¹ may also denote T¹, Z¹ to Z⁴ are independently of each other —O—, —S—, —CO—, —COO—, —OCO—, —O—COO—, —CO—NR⁰—, —NR⁰—CO—, —OCH₂—, —CH₂O—, —SCH₂—, —CH₂S—, —CF₂O—, —OCF₂—, —CF₂S—, —SCF₂—, —CH₂CH₂—, —CF₂CH₂—, —CH₂CF₂—, —CF₂CF₂—, —CH=N—, —N=CH—, —N=N—, —CH=CR⁰—, —CY¹=CY²—, —C≡C—, —CH=CH—COO—, —OCO—CH=CH— or a single bond, Y¹ and Y² are independently of each other H, F, Cl or CN, T¹ is a group consisting of 1 or 2 benzo[1,2-b:4,5-b'] dithiophene units which are optionally substituted by R¹, R¹ is H, halogen, CN, NO₂, straight chain, branched or cyclic alkyl with 1 to 20 C-atoms, which is unsubstituted, mono- or polysubstituted by F, Cl, Br, I or CN, and wherein one or more non-adjacent CH₂ groups are optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CY¹=CY²— or —C≡C— in such a manner that O and/or S atoms are not linked directly to one another, an aromatic or heteroaromatic group, or is P-Sp-X, R⁰ and R⁰⁰ are independently of each other H or alkyl with 1 to 12 C-atoms.

17. The reactive mesogenic benzodithiophene according to claim 5, wherein said mesogenic benzodithiophene is selected from the following formulae

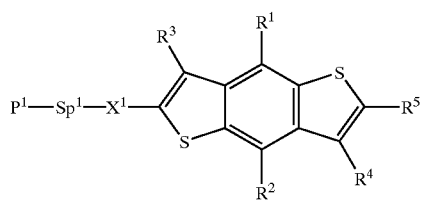
I1
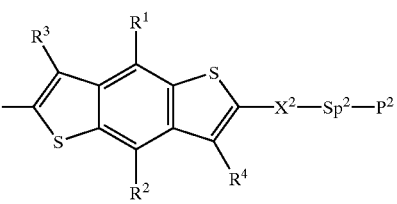
I2
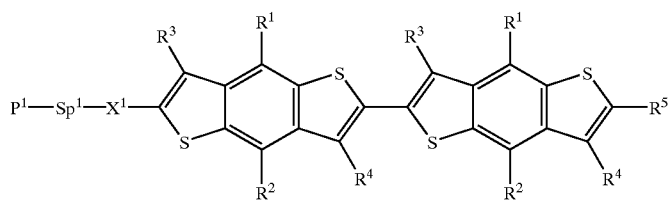
I3
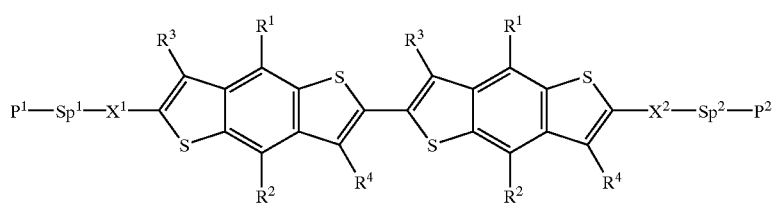
I4
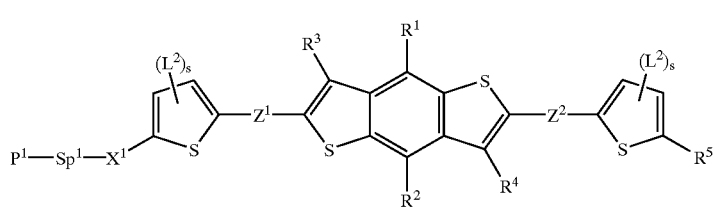
I5
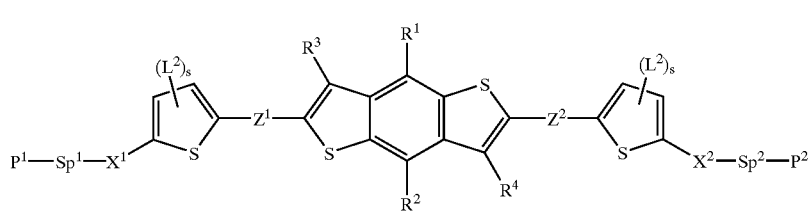
I6
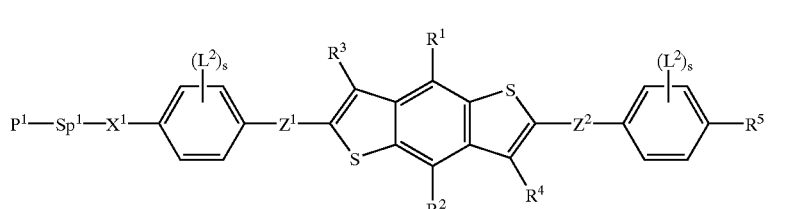
I7
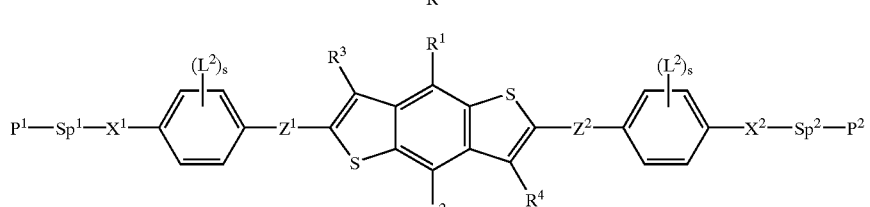
I8
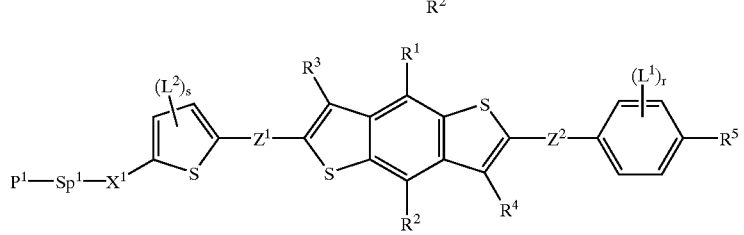
I9

-continued
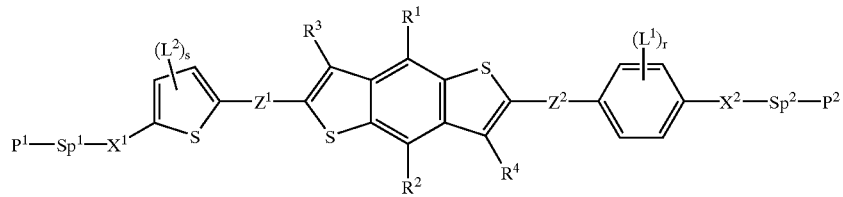
I10
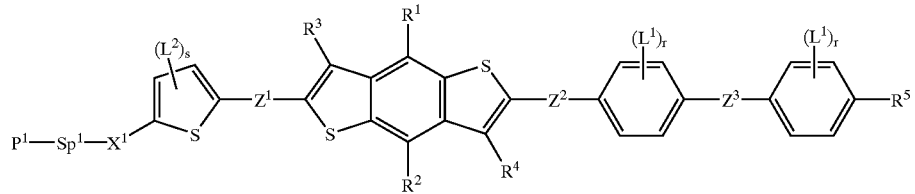
I11
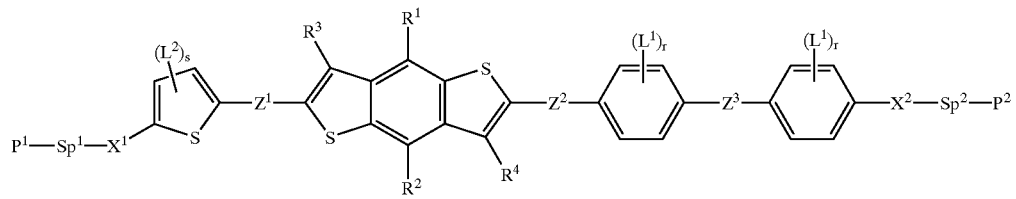
I12
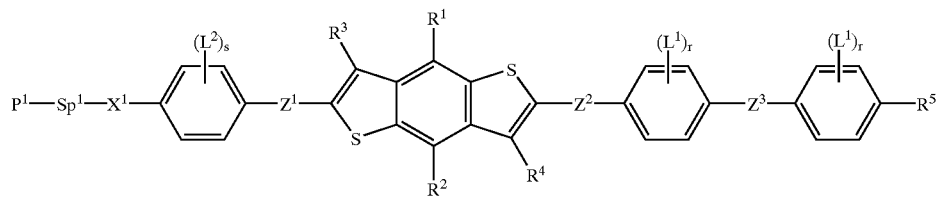
I13
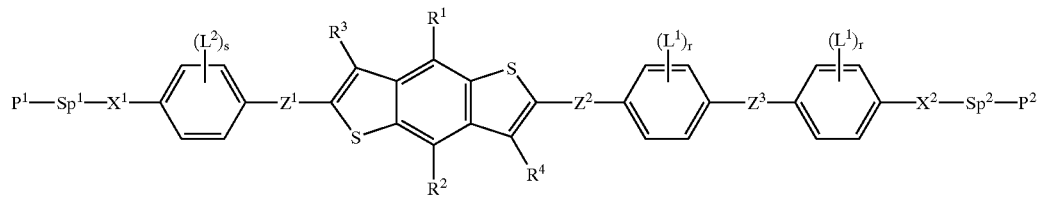
I14
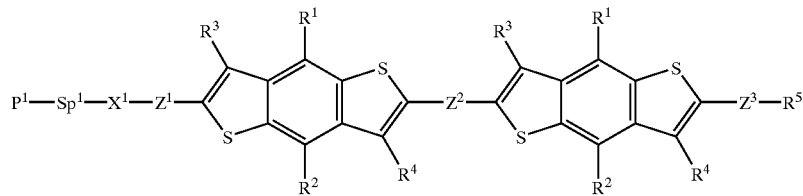
I15
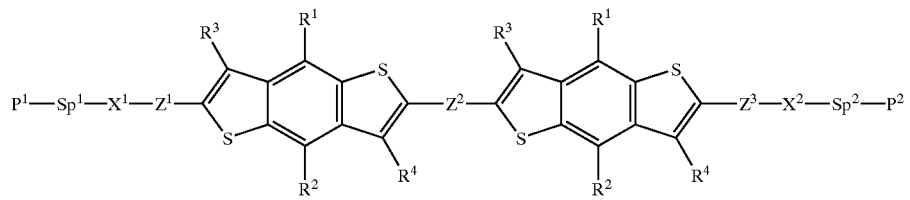
I16

-continued

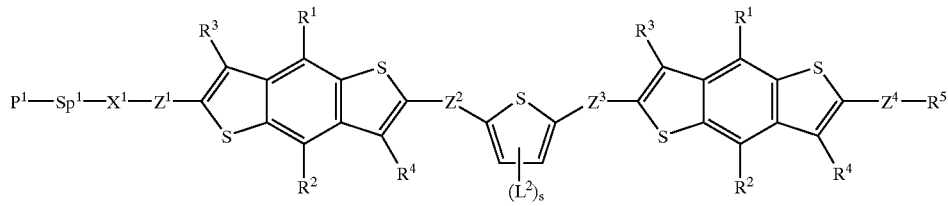

I17

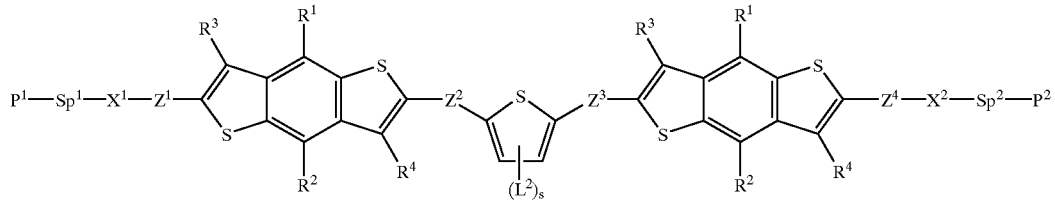

I18

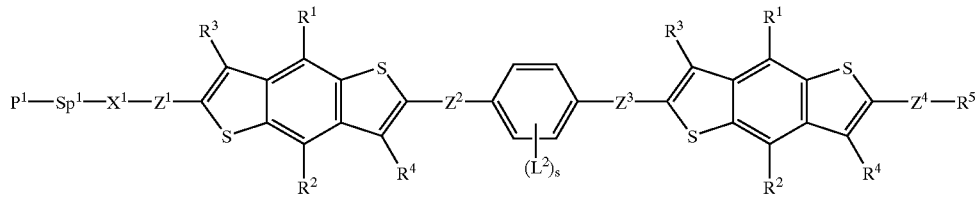

I19

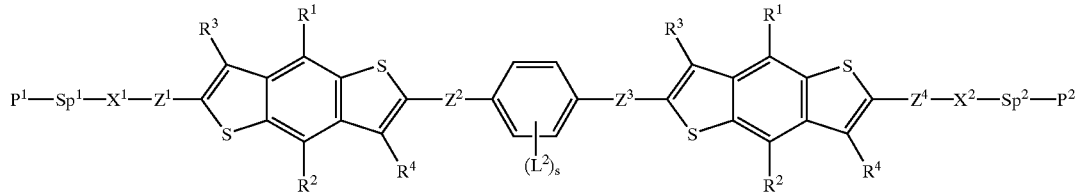

I20 wherein
- $P^1$ and $P^2$ are identical or different polymerisable or reactive group groups,
- $Sp^1$ and $Sp^2$ are identical or different and are selected from spacer groups and single bonds,
- $X^1$ and $X^2$ are identical or different and are selected from linkage groups and single bonds,
- $Z^1$ to $Z^4$ are independently of each other —O—, —S—, —CO—, —COO—, —OCO—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond,
- $R^1$ to $R^4$ are independently of one another one H, halogen CN, NO$_2$, straight chain, branched or cyclic alkyl with 1 to 20 C-atoms, which is unsubstituted, mono- or polysubstituted by F, Cl, Br, I or CN, and wherein one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CY$^1$=CY$^2$— or —C≡C— in such a manner that O and/or S atoms are not linked directly to one another, an aromatic or heteroaromatic group, or is P-Sp-X,
- $R^5$ is H, halogen CN, NO$_2$, straight chain, branched or cyclic alkyl with 1 to 20 C-atoms, which is unsubstituted, mono- or polysubstituted by F, Cl, Br, I or CN, and wherein one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CY$^1$=CY$^2$— or —C≡C— in such a manner that O and/or S atoms are not linked directly to one another, an aromatic or heteroaromatic group, or is P-Sp-X,
- $L^1$ is F, Cl, Br, CN, SCN, NO$_2$, SF$_5$ or an alkyl, alkoxy, alkylcarbonyl or alkoxycarbonyl group with 1 to 12 C atoms, wherein one or more H atoms are optionally replaced by F or Cl,
- $L^2$ is F, Cl, Br, GN, SCN, NO$_2$, SF$_5$ or an alkyl, alkoxy, alkylcarbonyl or alkoxycarbonyl group with 1 to 12 C atoms, wherein one or more H atoms are optionally replaced by F or Cl,
- r is 0, 1, 2, 3 or 4, and
- s is 0, 1 or 2.

18. The reactive mesogenic benzodithiophene according to claim 17, wherein $Z^1$ to $Z^4$ are independently of each other —CH=CH—, —CH=CF—, —CF=CH—, CH=CCl—, —CCl=CH—, —CF=CF—, —CCl=CCl—, —C≡C— or a single bond.

19. The reactive mesogenic benzodithiophene according to claim 17, wherein said at least one $R^1$ to $R^4$ are independently of each other a halogen atom.

20. The reactive mesogenic benzodithiophene according to claim 17, wherein said at least one $R^1$ to $R^4$ are independently of each other fluorinated alkyl groups with 1 to 15 C atoms.

21. The reactive mesogenic benzodithiophene according to claim 17, wherein said $R^5$ is a halogen or a fluorinated alkyl group with 1 to 15 C atoms.

22. The reactive mesogenic benzodithiophene according to claim 17, wherein said $L^1$ is F, Cl, or alkyl or alkoxy with 1 to 3 C-atoms that is optionally mono-, poly-, or perfluorinated.

23. The reactive mesogenic benzodithiophene according to claim 17, wherein said $L^2$ is alkyl with 1 to 12 C-atoms that is optionally mono-, poly-, or perfluorinated.

24. The reactive mesogenic benzodithiophene according to claim 5, wherein the polymerisable or reactive group or group P is selected from $CH_2=CW^1$-COO—,

$CH_2=CW^2$-$(O)_{k1}$—, $CH_3$—CH=CH—O—, $(CH_2=CH)_2CH$—OCO—, $(CH_2=CH$—$CH_2)_2CH$—OCO—, $(CH_2=CH)_2CH$—O—, $(CH_2=CH$—$CH_2)_2N$—, HO—$CW^2W^3$-, HS—$CW^2W^3$-, $HW^2N$—, HO—$CW^2W^3$-NH—, $CH_2=CW^1$—CO—NH—, $CH_2=CH$—$(COO)_{k1}$-Phe-$(O)_{k2}$—, Phe-CH=CH—, HOOC—, OCN—, and $W^4W^5W^6Si$—, $W^1$ is H, Cl, CN, phenyl or alkyl with 1 to 5 C-atoms,
  $W^2$ and $W^3$ are each independently of each other H or alkyl with 1 to 5 C-atoms,
  $W^4$, $W^5$ and $W^6$ are each independently of each other Cl, oxaalkyl or oxacarbonylalkyl with 1 to 5 C-atoms,
  Phe is 1,4-phenylene, and
  $k_1$ and $k_2$ are each independently of each other 0 or 1.

25. The reactive mesogenic benzodithiophene according to claim 1, wherein said mesogenic benzodithiophene exhibits a liquid crystal phase.

26. A reactive liquid crystal mixture comprising a reactive mesogenic benzodithiophene according to claim 1 and optionally one or more further reactive compounds wherein at least one of said benzodithiophenes or said further reactive compounds is mesogenic or liquid crystalline.

27. In a semiconductor or charge transport material for use in an optical device, electrooptical device, electronic device, a component of integrated circuitry, a field effect transistor (FET), thin film transistor in flat panel display applications, Radio Frequency Identification (RFID) tags, semiconducting components for organic light emitting diode (OLED) photovoltaic or sensor devices, electrode materials in batteries, photoconductors and for electrophotographic applications, the improvement wherein said material comprises a reactive material according to claim 26.

28. A side chain liquid crystal polymer obtained by polymerisation of one or more reactive materials of claim 26 or by grafting one or more of said reactive materials to a polymer backbone in a polymer-analogous reaction, optionally with one or more additional mesogenic or non-mesogenic comonomers.

29. A anisotropic polymer film with charge transport properties obtainable from a reactive liquid crystal mixture according to claim 26 that is aligned in its liquid crystal phase into macroscopically uniform orientation and polymerised or crosslinked to fix the oriented state.

30. In a semiconductor or charge transport material for use in an optical device, electrooptical device, electronic device, a component of integrated circuitry, a field effect transistor (FET), thin film transistor in flat panel display applications, Radio Frequency Identification (RFID) tags, semiconducting components for organic light emitting diode (OLED) photovoltaic or sensor devices, electrode materials in batteries, photoconductors and for electrophotographic applications, the improvement wherein said material comprises a polymer film according to claim 29.

31. A polymer film according to claim 29, wherein said polymer film is oxidatively doped to form a conducting ionic species.

32. A reactive material according to claim 26, wherein said material is oxidatively doped to form a conducting ionic species.

33. A side chain liquid crystal polymer obtained by polymerisation of one or more compounds of claim 1 or by grafting one or more of said compounds to a polymer backbone in a polymer-analogous reaction, optionally with one or more additional mesogenic or non-mesogenic comonomers.

34. In a semiconductor or charge transport material for use in an optical device, electrooptical device, electronic device, a component of integrated circuitry, a field effect transistor (FET), thin film transistor in flat panel display applications, Radio Frequency Identification (RFID) tags, semiconducting components for organic light emitting diode (OLED) photovoltaic or sensor devices, electrode materials in batteries, photoconductors and for electrophotographic applications, the improvement wherein said material comprises a polymer according to claim 33.

35. A polymer according to claim 33, wherein said polymer is oxidatively doped to form a conducting ionic species.

36. In a semiconductor or charge transport material for use in an optical device, electrooptical device, electronic device, a component of integrated circuitry, a field effect transistor (FET), thin film transistor in flat panel display applications, Radio Frequency Identification (RFID) tags, semiconducting components for organic light emitting diode (OLED) photovoltaic or sensor devices, electrode materials in batteries, photoconductors and for electrophotographic applications, the improvement wherein said material comprises a compound according to claim 1.

37. In a security marking or device comprising one or more mono-, oligo-, or polymers, the improvement wherein said marking or device comprises a FET or RFID tag according to claim 36.

38. In a field effect transistor, as a component of integrated circuitry, as a thin film transistor in flat panel display application, or in a Radio Frequency Identification (RFID) tag, the improvement wherein said transistor comprises a compound according to claim 1.

39. In a security marking or device comprising one or more mono-, oligo- or polymers, the improvement wherein said marking or device comprises a compound according to claim 1.

40. A compound according to claim 1, wherein said compound is oxidatively or reductively doped to form a conducting ionic species.

41. In a charge injection layer, planarising layer, antistatic film, conducting substrate, or pattern for electronic applications or flat panel displays, the improvement wherein said layer, film, substrate, or pattern comprises a compound according to claim 1.

42. A reactive mesogenic benzodithiophene according to claim 1, said central mesogenic core comprises one or more benzo[1,2-b:4,5-b']dithiophen-2,6-diyl and/or one or more [2,2']-bibenzo[1,2-b:4,5-b']dithiophen-6,6-diyl groups, which in each case is optionally mono- or polysubstituted by halogen CN, $NO_2$, straight chain, branched or cyclic alkyl with 1 to 20 C-atoms, which is unsubstituted, mono- or polysubstituted by F, Cl, Br, I or CN, and wherein one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CY$^1$=CY$^2$— or —C≡C— in such a manner that O and/or S atoms are not linked directly to one another, an aromatic or heteroaromatic group, or is P-Sp-X.

43. A reactive mesogenic benzodithiophene according to claim 42, further comprising unsaturated organic groups that form a conjugated system together with said one or more benzo[1,2-b:4,5-b']dithiophen-2,6-diyl and/or one or more [2,2']-bibenzo[1,2-b:4,5-b']dithiophen-6,6-diyl groups.

44. The reactive mesogenic benzodithiophene according to claim 43, wherein said mesogenic core is linked via a spacer group to said reactive groups.

45. The reactive mesogenic benzodithiophene according to claim 42, wherein said mesogenic core is linked via a spacer group to said reactive groups.

46. A reactive mesogenic benzodithiophene according to formula I

P-Sp-X-T-R    I wherein

P is a polymerisable or reactive group,

Sp is a spacer group or a single bond,

X is a linkage group or a single bond,

R is H, halogen, CN, NO$_2$, an aliphatic, alicyclic or aromatic group with up to 40 C atoms that optionally comprises one or more hetero atoms and wherein one or more rings can be fused, or P-Sp-X—, and T is a mesogenic group comprising one or more benzodithiophene groups, wherein the benzodithiophene groups benzo[1,2-b:4,5-b']dithiophene groups, selected from formula II -Z$^1$-(A$^1$-Z$^2$)$_m$-(T$^1$-Z$^3$)$_n$-(A$^2$-Z$^4$)$_o$-    II wherein A$^1$ and A$^2$ are independently of each other an aromatic, heteroaromatic or alicyclic group with up to 18 C atoms which is unsubstituted, mono- or polysubstituted with R$^1$, and A$^1$ may also denote T$^1$, Z$^1$ to Z$^4$ are independently of each other —O—, —S—, —CO—, —COO—, —OCO—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond, Y$^1$ and Y$^2$ are independently of each other H, F, Cl or CN, T$^1$ is a group consisting of 1 or 2 benzodithiophene units which are optionally substituted by R$^1$, R$^1$ is H, halogen, CN, NO$_2$, straight chain, branched or cyclic alkyl with 1 to 20 C-atoms, which is unsubstituted, mono- or polysubstituted by F, Cl, Br, I or CN, and wherein one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CY$^1$=CY$^2$— or —C≡C— in such a manner that O and/or S atoms are not linked directly to one another, an aromatic or heteroaromatic group, or P-Sp-X, R$^0$ and R$^{00}$ are independently of each other H or alkyl with 1 to 12 C-atoms, m and o are independently of each other 0, 1, 2 or 3, and n is 1, 2 or 3, wherein at least one of said benzodithiophene units of T$^1$ is substituted by R$^1$.

47. In a semiconductor or charge transport material for use in an optical device, electrooptical device, electronic device, a component of integrated circuitry, a field effect transistor (FET), thin film transistor in flat panel display applications, Radio Frequency Identification (RFID) tags, semiconducting components for organic light emitting diode (OLED) photovoltaic or sensor devices, electrode materials in batteries, photoconductors and for electrophotographic applications, the improvement wherein said material comprises a reactive mesogenic benzodithiophene comprising a central mesogenic core comprising one or more benzodithiophene groups, wherein the benzodithiophene groups benzo[1,2-b:4,5-b']dithiophene groups, linked to one or more reactive groups.

48. A side chain liquid crystal polymer obtained by polymerisation of one or more reactive mesogenic benzodithiophene compounds, wherein the benzodithiophene groups benzo[1,2-b:4,5-b']dithiophene compounds, having a central mesogenic core comprising one or more benzodithiophene groups linked to one or more reactive groups, or by grafting one or more of said compounds to a polymer backbone in a polymer-analogous reaction, optionally with one or more additional mesogenic or non-mesogenic comonomers.

49. A polymer according to claim 48, wherein said polymer is oxidatively doped to form a conducting ionic species.

50. A side chain liquid crystal polymer obtained by polymerisation of a reactive liquid crystal mixture comprising a reactive mesogenic benzodithiophene having a central mesogenic core comprising one or more benzodithiophene groups linked to one or more reactive groups and one or more further reactive compounds wherein at least one of said benzodithiophenes or said further reactive compounds is mesogenic or liquid crystalline, or by grafting said reactive mesogenic benzodithiophene and said one or more further reactive compounds to a polymer backbone in a polymer-analogous reaction, optionally with one or more additional mesogenic or non-mesogenic comonomers.

* * * * *

UNITED STATES PATENT AND TRADEMARK OFFICE
CERTIFICATE OF CORRECTION

PATENT NO. : 6,913,710 B2
DATED : July 5, 2005
INVENTOR(S) : Louise Farrand et al.

It is certified that error appears in the above-identified patent and that said Letters Patent is hereby corrected as shown below:

Column 25,
Line 36, "–$OCH_2$–, –$CH_2O$–, –$SCH_2$–, –$CH_2S$–" should read -- $SCH_2$–, –$CH_2S$– --.

Column 26,
Lines 32 and 52, "–CH=CH, –" should read -- –CH=CH–, --.
Line 37, "diothiophene" should read -- dithiophene --.

Column 27,
Line 37, "–CH=CH, –" should read -- –CH=CH–, --.
Line 48, "furan 2,5 diyl" should read -- furan-2,5-diyl --.

Column 28,
Line 1, "–CH=CH, –" should read -- –CH=CH–, --.

Column 33,
Line 39, "group groups" should read -- groups --.
Line 54, "one another one H" should read -- one another H --.
Line 66, "halogen" should read -- halogen, --.

Column 34,
Line 50, "GN" should read -- CN --.

Column 35,
Line 57, "A anisotropic" should read -- An anisotropic --.

Column 36,
Line 65, "halogen CN," should read -- halogen, CN, --.

Column 37,
Line 36, "groups benzo" should read -- groups are benzo --.

UNITED STATES PATENT AND TRADEMARK OFFICE
CERTIFICATE OF CORRECTION

PATENT NO.   : 6,913,710 B2
DATED        : July 5, 2005
INVENTOR(S)  : Louise Farrand et al.

It is certified that error appears in the above-identified patent and that said Letters Patent is hereby corrected as shown below:

<u>Column 38,</u>
Lines 29-30, "groups benzo" should read -- groups are benzo --.
Line 35, "groups benzo" should read -- compounds are benzo --.

Signed and Sealed this

Second Day of May, 2006

JON W. DUDAS
*Director of the United States Patent and Trademark Office*